US012228492B2

(12) United States Patent
Kim et al.

(10) Patent No.: US 12,228,492 B2
(45) Date of Patent: *Feb. 18, 2025

(54) COMPOSITIONS AND METHODS FOR CELL-LIKE CALIBRATION PARTICLES

(71) Applicant: Slingshot Biosciences, Inc., Emeryville, CA (US)

(72) Inventors: Jeffrey Kim, Berkeley, CA (US); Anh Tuan Nguyen, San Francisco, CA (US); Brandon Miller, Oakland, CA (US)

(73) Assignee: Slingshot Biosciences, Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/731,774

(22) Filed: Jun. 3, 2024

(65) Prior Publication Data
US 2024/0319067 A1    Sep. 26, 2024

Related U.S. Application Data

(63) Continuation of application No. 18/213,934, filed on Jun. 26, 2023, now Pat. No. 12,038,369, which is a continuation of application No. 17/727,879, filed on Apr. 25, 2022, now Pat. No. 11,726,023, which is a continuation of application No. 17/155,294, filed on Jan. 22, 2021, now Pat. No. 11,313,782.

(60) Provisional application No. 62/965,494, filed on Jan. 24, 2020.

(51) Int. Cl.
*G01N 15/10* (2024.01)

(52) U.S. Cl.
CPC . *G01N 15/1012* (2013.01); *G01N 2015/1006* (2013.01); *G01N 2015/1014* (2024.01)

(58) Field of Classification Search
CPC ....... G01N 15/1012; G01N 2015/1006; G01N 2015/1014; G01N 2015/1018
See application file for complete search history.

(56) References Cited

U.S. PATENT DOCUMENTS

| 3,822,095 A | 7/1974 | Hirschfeld |
| 3,872,312 A | 3/1975 | Hirschfeld |
| 3,916,205 A | 10/1975 | Kleinerman |
| 3,937,799 A | 2/1976 | Lewin et al. |

(Continued)

FOREIGN PATENT DOCUMENTS

| CN | 101214217 A | 7/2008 |
| CN | 101245368 A | 8/2008 |

(Continued)

OTHER PUBLICATIONS

Atkin-Smith et al., "Isolation of cell type-specific apoptotic bodies by fluorescence-activated cell sorting," Scientific Reports, vol. 7, No. 1, Feb. 1, 2017, pp. 1-7.

(Continued)

*Primary Examiner* — Paul M. West
(74) *Attorney, Agent, or Firm* — COOLEY LLP

(57) ABSTRACT

A method includes calibrating a cytometric device for analysis of a target cell, by inserting, into the cytometric device, a hydrogel particle. The hydrogel particle has at least one of a background fluorescent property or a spectral property that is substantially similar to the at least one of a background fluorescent property or a spectral property of the target cell. The method also includes measuring at least one property of the hydrogel particle using the cytometric device.

30 Claims, 19 Drawing Sheets

(56) References Cited

U.S. PATENT DOCUMENTS

| | | |
|---|---|---|
| 3,947,564 A | 3/1976 | Shannon et al. |
| 3,975,084 A | 8/1976 | Block |
| 4,271,123 A | 6/1981 | Curry et al. |
| 4,295,199 A | 10/1981 | Curry et al. |
| 4,389,491 A | 6/1983 | Hanamoto et al. |
| 4,409,335 A | 10/1983 | Hanamoto et al. |
| 4,448,888 A | 5/1984 | Bleile et al. |
| 4,511,662 A | 4/1985 | Baran et al. |
| 4,704,891 A | 11/1987 | Recktenwald et al. |
| 4,774,189 A | 9/1988 | Schwartz |
| 4,857,451 A | 8/1989 | Schwartz |
| 5,093,234 A | 3/1992 | Schwartz |
| 5,244,799 A | 9/1993 | Anderson |
| 5,283,079 A | 2/1994 | Wang et al. |
| 5,395,688 A | 3/1995 | Wang et al. |
| 5,820,879 A | 10/1998 | Fernandez et al. |
| 5,841,139 A | 11/1998 | Sostek et al. |
| 5,871,722 A | 2/1999 | Nacht et al. |
| 5,888,823 A | 3/1999 | Matsumoto et al. |
| 6,043,506 A | 3/2000 | Heffelfinger et al. |
| 6,107,365 A | 8/2000 | Bertozzi et al. |
| 6,108,082 A | 8/2000 | Pettipiece et al. |
| 6,214,539 B1 | 4/2001 | Cosand |
| 6,280,618 B2 | 8/2001 | Watkins et al. |
| 6,372,813 B1 | 4/2002 | Johnson et al. |
| 6,516,537 B1 | 2/2003 | Teich et al. |
| 6,586,176 B1 | 7/2003 | Trnovsky et al. |
| 6,657,030 B2 | 12/2003 | Vanderbilt |
| 6,762,055 B2 | 7/2004 | Carver et al. |
| 6,806,058 B2 | 10/2004 | Jesperson et al. |
| 6,872,578 B2 | 3/2005 | Watkins et al. |
| 6,897,072 B1 | 5/2005 | Rich et al. |
| 7,045,366 B2 | 5/2006 | Huang et al. |
| RE39,542 E | 4/2007 | Jain et al. |
| 7,205,156 B2 | 4/2007 | Rich et al. |
| 7,294,503 B2 | 11/2007 | Quake et al. |
| 7,314,584 B2 | 1/2008 | Tsutsui et al. |
| 7,465,538 B2 | 12/2008 | Watkins et al. |
| 7,479,631 B2 | 1/2009 | Rich et al. |
| 7,482,161 B2 | 1/2009 | Carver et al. |
| 7,482,167 B2 | 1/2009 | Sammak et al. |
| 7,531,357 B2 | 5/2009 | Carver et al. |
| 7,569,399 B2 | 8/2009 | Watkins et al. |
| 7,588,942 B2 | 9/2009 | Ho et al. |
| 7,601,539 B2 | 10/2009 | Kawate |
| 7,776,927 B2 | 8/2010 | Chu et al. |
| 7,842,498 B2 | 11/2010 | Um et al. |
| 8,030,095 B2 | 10/2011 | Harriman |
| 8,105,845 B2 | 1/2012 | Notcovich et al. |
| 8,114,580 B2 | 2/2012 | Carver et al. |
| 8,187,885 B2 | 5/2012 | Purvis, Jr. |
| 8,415,161 B2 | 4/2013 | Yan et al. |
| 8,415,173 B2 | 4/2013 | Harriman |
| 8,451,450 B2 | 5/2013 | Heng |
| 8,580,530 B2 | 11/2013 | Buffiere et al. |
| 8,580,531 B2 | 11/2013 | Buffiere et al. |
| 8,603,828 B2 | 12/2013 | Walker et al. |
| 8,609,363 B2 | 12/2013 | Heng et al. |
| 8,704,158 B2 | 4/2014 | Haberstroh et al. |
| 8,748,183 B2 | 6/2014 | Durack et al. |
| 9,012,167 B2 | 4/2015 | Dallenne et al. |
| 9,110,050 B2 | 8/2015 | Likuski et al. |
| 9,175,421 B2 | 11/2015 | Notcovich et al. |
| 9,176,154 B2 | 11/2015 | Darmstadt et al. |
| 9,213,034 B2 | 12/2015 | Walker et al. |
| 9,217,175 B2 | 12/2015 | Regan et al. |
| 9,228,898 B2 | 1/2016 | Kiani et al. |
| 9,417,190 B2 | 8/2016 | Hindson et al. |
| 9,476,101 B2 | 10/2016 | Pregibon et al. |
| 9,658,220 B2 | 5/2017 | King et al. |
| 9,696,257 B2 | 7/2017 | Fox et al. |
| 9,714,897 B2 | 7/2017 | Kim et al. |
| 9,804,149 B2 | 10/2017 | Darmstadt et al. |
| 9,816,931 B2 | 11/2017 | Abate et al. |
| 9,915,598 B2 | 3/2018 | Kim et al. |
| 10,067,135 B2 | 9/2018 | Kaul et al. |
| 10,180,385 B2 | 1/2019 | Fox et al. |
| 10,191,039 B2 | 1/2019 | King et al. |
| 10,343,167 B2 | 7/2019 | Esmail et al. |
| 10,344,100 B1 | 7/2019 | Vashist et al. |
| 10,392,557 B2 | 8/2019 | Chan |
| 10,416,070 B1 | 9/2019 | Handique |
| 10,429,291 B2 | 10/2019 | Fox et al. |
| 10,481,068 B2 | 11/2019 | Kim et al. |
| 10,508,990 B2 | 12/2019 | Fox et al. |
| 10,732,189 B2 | 8/2020 | Buffiere et al. |
| 10,753,846 B2 | 8/2020 | Kim et al. |
| 10,942,109 B2 | 3/2021 | Kim et al. |
| 11,047,845 B1 | 6/2021 | Barry, Jr. et al. |
| 11,085,036 B2 | 8/2021 | Norberg et al. |
| 11,118,217 B2 | 9/2021 | Xue et al. |
| 11,155,809 B2 | 10/2021 | Lebofsky |
| 11,180,752 B2 | 11/2021 | Wu et al. |
| 11,186,862 B2 | 11/2021 | Lebofsky et al. |
| 11,213,490 B2 | 1/2022 | Shoichet et al. |
| 11,231,355 B2 | 1/2022 | Handique |
| 11,274,337 B2 | 3/2022 | Xue et al. |
| 11,300,496 B2 | 4/2022 | Handique |
| 11,313,782 B2 | 4/2022 | Kim et al. |
| 11,479,816 B2 | 10/2022 | Lebofsky et al. |
| 11,506,655 B2 | 11/2022 | Hunsley et al. |
| 11,598,768 B2 | 3/2023 | Kim |
| 11,603,556 B2 | 3/2023 | Lebofsky |
| 11,663,717 B2 | 5/2023 | Barnes et al. |
| 11,686,661 B2 | 6/2023 | Kim et al. |
| 11,726,023 B2 | 8/2023 | Kim et al. |
| 11,747,261 B2 | 9/2023 | Kim et al. |
| 11,761,877 B2 | 9/2023 | Kim et al. |
| 12,038,369 B2 | 7/2024 | Kim et al. |
| 12,066,369 B2 | 8/2024 | Kim et al. |
| 2001/0008217 A1 | 7/2001 | Watkins et al. |
| 2001/0054580 A1 | 12/2001 | Watkins et al. |
| 2002/0115116 A1 | 8/2002 | Song et al. |
| 2003/0013116 A1 | 1/2003 | Song et al. |
| 2003/0022157 A1 | 1/2003 | Zauderer et al. |
| 2003/0064403 A1 | 4/2003 | Song et al. |
| 2003/0124371 A1 | 7/2003 | Um et al. |
| 2003/0132538 A1 | 7/2003 | Chandler |
| 2003/0190749 A1 | 10/2003 | Surger et al. |
| 2003/0218130 A1 | 11/2003 | Boschetti et al. |
| 2003/0224444 A1 | 12/2003 | Sabbadini et al. |
| 2004/0126904 A1 | 7/2004 | Watkins et al. |
| 2005/0059086 A1 | 3/2005 | Huang et al. |
| 2005/0090016 A1 | 4/2005 | Rich et al. |
| 2005/0112650 A1 | 5/2005 | Chang et al. |
| 2005/0118230 A1 | 6/2005 | Hill et al. |
| 2005/0172476 A1 | 8/2005 | Stone et al. |
| 2005/0176056 A1 | 8/2005 | Sammak et al. |
| 2005/0208573 A1 | 9/2005 | Bell et al. |
| 2006/0163385 A1 | 7/2006 | Link et al. |
| 2006/0223187 A1 | 10/2006 | Carver et al. |
| 2006/0240560 A1 | 10/2006 | Bakker et al. |
| 2006/0250616 A1 | 11/2006 | Pettipiece et al. |
| 2006/0269962 A1 | 11/2006 | Watkins et al. |
| 2006/0275820 A1 | 12/2006 | Watkins et al. |
| 2007/0003442 A1 | 1/2007 | Link et al. |
| 2007/0054119 A1 | 3/2007 | Garstecki et al. |
| 2007/0082019 A1 | 4/2007 | Huang et al. |
| 2007/0087348 A1 | 4/2007 | Notcovich et al. |
| 2007/0158547 A1 | 7/2007 | Rich et al. |
| 2007/0178168 A1 | 8/2007 | Ho et al. |
| 2007/0254378 A1 | 11/2007 | Zhang et al. |
| 2007/0259415 A1 | 11/2007 | Zigova et al. |
| 2008/0014589 A1 | 1/2008 | Link et al. |
| 2008/0019921 A1 | 1/2008 | Zhang |
| 2008/0023630 A1 | 1/2008 | Boschetti et al. |
| 2008/0026468 A1 | 1/2008 | Carver et al. |
| 2008/0032405 A1 | 2/2008 | Ho et al. |
| 2008/0044472 A1 | 2/2008 | Garcia et al. |
| 2008/0090737 A1 | 4/2008 | Boschetti |
| 2009/0148961 A1 | 6/2009 | Luchini et al. |
| 2010/0120059 A1 | 5/2010 | Yan et al. |
| 2010/0178647 A1 | 7/2010 | Carver et al. |
| 2010/0178656 A1 | 7/2010 | Buffiere et al. |

(56) References Cited

U.S. PATENT DOCUMENTS

| | | |
|---|---|---|
| 2010/0184101 A1 | 7/2010 | Buffiere et al. |
| 2010/0187441 A1 | 7/2010 | Waldbeser et al. |
| 2010/0234252 A1 | 9/2010 | Moradi-Araghi et al. |
| 2010/0285594 A1 | 11/2010 | Purvis, Jr. |
| 2011/0117670 A1 | 5/2011 | Walker et al. |
| 2011/0218123 A1 | 9/2011 | Weitz et al. |
| 2011/0222068 A1 | 9/2011 | Heng |
| 2011/0318820 A1 | 12/2011 | Hinz et al. |
| 2012/0129723 A1 | 5/2012 | Notcovich et al. |
| 2012/0295300 A1 | 11/2012 | Heng et al. |
| 2012/0309651 A1 | 12/2012 | Pregibon et al. |
| 2013/0089883 A1 | 4/2013 | Dallenne et al. |
| 2013/0177973 A1 | 7/2013 | Kondo |
| 2013/0274125 A1 | 10/2013 | Binder et al. |
| 2014/0073532 A1 | 3/2014 | Walker et al. |
| 2014/0100791 A1 | 4/2014 | Darmstadt et al. |
| 2014/0157859 A1 | 6/2014 | Darmstadt et al. |
| 2014/0179808 A1 | 6/2014 | Flanagan |
| 2014/0198313 A1 | 7/2014 | Tracy et al. |
| 2014/0221238 A1 | 8/2014 | Regan et al. |
| 2014/0377334 A1 | 12/2014 | Irvine et al. |
| 2015/0027207 A1 | 1/2015 | Likuski et al. |
| 2015/0094232 A1 | 4/2015 | Abate et al. |
| 2015/0177115 A1 | 6/2015 | Kim et al. |
| 2015/0211044 A1 | 7/2015 | Dallenne et al. |
| 2015/0267196 A1 | 9/2015 | Alsberg et al. |
| 2016/0258856 A1 | 9/2016 | Kim et al. |
| 2017/0045436 A1 | 2/2017 | Fox et al. |
| 2017/0159132 A1 | 6/2017 | Okino et al. |
| 2017/0268998 A1 | 9/2017 | Fox et al. |
| 2017/0361322 A1 | 12/2017 | Esmail et al. |
| 2017/0370951 A1 | 12/2017 | Buffiere et al. |
| 2018/0172687 A1 | 6/2018 | Kaul et al. |
| 2018/0216171 A1 | 8/2018 | Xue et al. |
| 2018/0275040 A1 | 9/2018 | Kim et al. |
| 2018/0371525 A1 | 12/2018 | Lebofsky et al. |
| 2019/0145881 A1 | 5/2019 | Fox et al. |
| 2019/0154707 A1 | 5/2019 | Flamini et al. |
| 2019/0249171 A1 | 8/2019 | Wu et al. |
| 2019/0293546 A1 | 9/2019 | Handique |
| 2020/0056231 A1 | 2/2020 | Lebofsky et al. |
| 2020/0085971 A1 | 3/2020 | Kevlahan et al. |
| 2020/0115675 A1 | 4/2020 | Pathak et al. |
| 2020/0150020 A1 | 5/2020 | Kim et al. |
| 2020/0206145 A1 | 7/2020 | Shi et al. |
| 2020/0209064 A1 | 7/2020 | Owsley et al. |
| 2020/0232979 A1 | 7/2020 | Revzin et al. |
| 2020/0249242 A1 | 8/2020 | Batxelli-Molina et al. |
| 2020/0332354 A1 | 10/2020 | Xue et al. |
| 2020/0363434 A1 | 11/2020 | Buffiere et al. |
| 2020/0399428 A1 | 12/2020 | Kleine-Brüggeney et al. |
| 2020/0400546 A1 | 12/2020 | Kim et al. |
| 2020/0408747 A1 | 12/2020 | Zur Megede et al. |
| 2021/0040567 A1 | 2/2021 | Handique et al. |
| 2021/0130880 A1 | 5/2021 | Lebofsky |
| 2021/0190740 A1 | 6/2021 | Scolari et al. |
| 2021/0231552 A1 | 7/2021 | Kim et al. |
| 2021/0247294 A1 | 8/2021 | Handique |
| 2021/0341469 A1 | 11/2021 | Kim et al. |
| 2022/0042077 A1 | 2/2022 | Lebofsky et al. |
| 2022/0065878 A1 | 3/2022 | Lee |
| 2022/0154266 A1 | 5/2022 | Xue et al. |
| 2022/0178810 A1 | 6/2022 | Kim et al. |
| 2022/0213530 A1 | 7/2022 | Larson et al. |
| 2022/0260476 A1 | 8/2022 | Kim et al. |
| 2022/0364976 A1 | 11/2022 | Kim et al. |
| 2023/0012786 A1 | 1/2023 | Lebofsky et al. |
| 2023/0062518 A1 | 3/2023 | Ebrahim et al. |
| 2023/0067460 A1 | 3/2023 | Nguyen et al. |
| 2023/0152202 A1 | 5/2023 | Kim et al. |
| 2023/0176042 A1 | 6/2023 | Kim et al. |
| 2023/0266223 A1 | 8/2023 | Kim et al. |
| 2024/0060038 A1 | 2/2024 | Nguyen et al. |
| 2024/0219382 A1 | 7/2024 | Ahn et al. |

FOREIGN PATENT DOCUMENTS

| | | |
|---|---|---|
| CN | 103744185 A | 4/2014 |
| CN | 104641217 A | 5/2015 |
| EP | 3585364 A1 | 1/2020 |
| JP | H07196916 A | 8/1995 |
| JP | 2002510541 A | 4/2002 |
| JP | 2007114026 A | 5/2007 |
| JP | 2012011269 A | 1/2012 |
| JP | 2013520530 A | 6/2013 |
| JP | 2013155358 A | 8/2013 |
| JP | 2014508516 A | 4/2014 |
| WO | WO-8910566 A1 | 11/1989 |
| WO | WO-0008212 A1 | 2/2000 |
| WO | WO-0132829 A2 | 5/2001 |
| WO | WO-03000014 A2 | 1/2003 |
| WO | WO-2005013896 A2 | 2/2005 |
| WO | WO-2006003423 A2 | 1/2006 |
| WO | WO-2006078841 A1 | 7/2006 |
| WO | WO-2006096571 A2 | 9/2006 |
| WO | WO-2008115653 A2 | 9/2008 |
| WO | WO-2008121342 A2 | 10/2008 |
| WO | WO-2010025190 A1 | 3/2010 |
| WO | WO-2010025988 A1 | 3/2010 |
| WO | WO-2011098407 A1 | 8/2011 |
| WO | WO-2012033811 A1 | 3/2012 |
| WO | WO-2013113670 A1 | 8/2013 |
| WO | WO-2018108341 A1 | 6/2018 |
| WO | WO-2020037214 A1 | 2/2020 |
| WO | WO-2021154900 A1 | 8/2021 |

OTHER PUBLICATIONS

Bele, Marjan, Olavi Siiman and Egon Matjevic, "Preparation and flow cytometry of uniform silica-fluorescent dye microspheres." Journal of colloid and interface science 254(2):274-282 (2002).

Chen, M., et al., "Initiator caspases in apoptosis signaling pathways", Apoptosis (London), Aug. 1, 2002, pp. 313-319, DOI: 10.1023/A:1016167228059.

Co-pending U.S. Appl. No. 18/417,986, inventors Jeffrey; Kim et al., filed on Jan. 19, 2024.

Extended European Search Report for European Application No. EP21744765.5 dated Jan. 29, 2024, 8 pages.

Extended European Search Report issued by the European Patent Office for Application No. 16749674.4, dated Sep. 6, 2018, 12 pages.

Gaulding, et al., "Reversible Inter- and Intra-microgel Cross-linking Using Disulfides," Macromolecules, 2012, vol. 45(1), pp. 39-45.

Hasegawa, Urara et al. "Nanogel-quantum dot hybrid nanoparticles for live cell imaging." Biochemical and biophysical research communications 331(4):917-921 (2005).

Higuchi, A., et al., "Design of polymeric materials for culturing human pluripotent stem cells: Progress toward feeder-free and xeno-free culturing," Progress in Polymer Science, Jul. 2014, vol. 39 (7), pp. 1348-1374.

International Search Report and Written Opinion for International Application No. PCT/US2022/048283 dated Feb. 14, 2023, 14 pages.

International Search Report and Written Opinion for International Patent Application No. PCT/US2016/017029, mailed May 19, 2016, 8 pages.

International Search Report and Written Opinion for International Patent Application No. PCT/US21/014538, dated Apr. 8, 2021, 19 pages.

International Search Report and Written Opinion for International Patent Application No. PCT/US21/030590, dated Jul. 26, 2021, 13 pages.

International Search Report and Written Opinion for PCT Application No. PCT/US2023/066684 dated Aug. 7, 2023, 15 pages.

International Search Report and Written Opinion for PCT Application No. PCT/US2023/067893 dated Oct. 10, 2023, 22 pages.

Jain et al. Zwitterionic Hydrogels Based on a Degradable Disulfide Carboxybetaine Cross-Linker, Langmuir 2019, 35, 1864-1871 (Year: 2019).

(56) References Cited

OTHER PUBLICATIONS

Jin et al., "Overview of cell death 1-124 signaling pathways", Cancer Biology &G Therapy, vol. 4, No. 2, Feb. 2, 2005, pp. 147-171, DOI: 10.4161/cbt.4.2.1508.

Kim, Jin-Woong et al., "Fabrication of Monodisperse Gel Shells and Functional Microgels in Microfluidic Devices," Angew. Chem. Int. Ed. 46:819-1822 (2007).

Lee, Ki-Chang and Lee, Sang-Yun, "Preparation of Highly Cross-Linked, Monodisperse Poly (methyl methacrylate) Microspheres by Dispersion Polymerization; Part II. Semi-continuation Processes," Macromolecular Research 6(4):293-302 (2008).

Liu, A.L., et al., "Methods for Generating Hydrogel Particles for Protein Delivery," Annals of Biomedical Engineering, Jun. 2016, vol. 44 (6), pp. 1946-1958.

Liu, Z. et al., Recent Advances on Magnetic Sensitive Hydrogels in Tissue Engineering, Frontiers in Chemistry, vol. 8 , Article 124, pp. 1-17, (Mar. 2020).

Luchini, Alessandra et al. "Smart hydrogel particles: biomarker harvesting: one-step affinity purification, size exclusion, and protection against degradation." Nano letters 8(1): 350-361 (2008).

Patanarut, Alexis et al., "Synthesis and characterization of hydrogel particles containing Cibacron Blue F3G-A." Colloids and Surfaces A: Physicochemical and Engineering Aspects 362(1):8-19 (2010).

Perez-Luna, V.H., et al., "Encapsulation of Biological Agents in Hydrogels for Therapeutic Applications," Gels, vol. 4(61), pp. 1-30, (Jul. 11, 2018).

Proll, Guenther et al. "Potential of label-free detection in high-content-screening applications." Journal of Chromatography A 1116(1):2-8 (2007).

Shastri, V.P., et al., "Non-Degradable Biocompatible Polymers in Medicine: Past, Present and Future", Current Pharmaceutical Biotechnology, Bentham Science Publishers, NL, vol. 4, No. 5, Jan. 1, 2003, pp. 331-337.

Tomczak, Nikodem et al., "Designer polymer-quantum dot architectures." Progress in Polymer Science 34:393-430 (2009).

Ugelstad, J. and Mork, P.C., "Swelling of Oligomer-Polymer Particles. New Methods of Preparation of Emulsions and Polymer Dispersions," Advances in Colloid and Interface Sciences, 13:101-140 (1980).

Wallberg et al., "Analysis of Apoptosis and Necroptosis by Fluorescence-Activated Cell Sorting," Cold Spring Harbor Protocol, vol. 2016, No. 4, Apr. 1, 2016, 7 pages.

| | | | | | | |
|---|---|---|---|---|---|---|
| Hydrogel Compensation Beads | APC | 0.90% | 0.00% | Known Compensation Beads | APC | 11.00% | -0.19% |
| | | 0.26% | 0.25% | | | -1.25% | 5.00% |
| | BV650 | BUV737 | APC-Cy7 | | BV650 | BUV737 | APC-Cy7 |

FIG. 11D

| % resonant co-monomer additive | Autofluorescence (mean intensity A.U. FL7A - BV510A channel) |
|---|---|
| 1% | 651 (low) |
| 5% | 1050 (Cell-like) |
| 10% | 4509 |
| Polystyrene control | 9781 (high) |
| Cellular control | 1052 |

| Crosslinking density | Autofluorescence (mean intensity A.U. FL7A - BV510A channel) |
|---|---|
| 1% | 703 |
| 10% | 1104 (Cell-like) |
| 40% | 5120 |
| Polystyrene control | 9781 (high) |
| Cellular control | 1052 |

FIG. 12

COMPOSITIONS AND METHODS FOR CELL-LIKE CALIBRATION PARTICLES

CROSS-REFERENCE TO RELATED APPLICATIONS

This application is a continuation of U.S. patent application Ser. No. 18/213,934, titled "Compositions and Methods for Cell-Like Calibration Particles," filed Jun. 26, 2023, which is a continuation of U.S. patent application Ser. No. 17/727,879, titled "Compositions and Methods for Cell-Like Calibration Particles," filed Apr. 25, 2022, now U.S. Pat. No. 11,726,023, which is a continuation of U.S. patent application Ser. No. 17/155,294, titled "Compositions and Methods for Cell-Like Calibration Particles," filed Jan. 22, 2021, now U.S. Pat. No. 11,313,782, which claims priority to and benefit of U.S. Provisional Application No. 62/965,494, filed Jan. 24, 2020 and titled "Compositions and Methods for Cell-Like Calibration Particles," the entire disclosures of each of which are incorporated by reference herein in their entireties.

This application is related to U.S. Pat. No. 9,915,598, issued Mar. 13, 2018 and titled "Hydrogel Particles with Tunable Optical Properties," and is related to U.S. Pat. No. 9,714,897, issued Jul. 25, 2017 and titled "Hydrogel Particles with Tunable Optical Properties and Methods for Using the Same," the entire disclosures of each of which are incorporated by reference herein for all purposes.

FIELD

The present disclosure relates to flow cytometry, and more specifically, to hydrogel bead substrates that exhibit cell-like autofluorescence, enabling more accurate fluorescence and spectral calibration and compensation.

BACKGROUND

Flow cytometry and hematology analysis are techniques that allow for the rapid separation, counting, and characterization of individual cells and are routinely used in clinical and laboratory settings for a variety of applications. The technology relies on directing a beam of light onto a focused stream of liquid. In some implementations, a number of detectors are then aimed at the point where the stream passes through the light beam: one detector in line with the light beam (forward scatter, or "FSC") and several detectors perpendicular to the light beam (side scatter, or "SSC"). FSC generally correlates with the cell volume and SSC depends on the inner complexity, or granularity, of the particle (i.e., shape of the nucleus, the amount and type of cytoplasmic granules or the membrane roughness). As a result of these correlations, different specific cell types exhibit different FSC and SSC, allowing cell types to be distinguished in flow cytometry. These measurements form the basis of cytometric analysis. In other forms of cytometry, cells are imaged and the descriptive features of the cells, such as size/shape/volume and, in some cases, biochemical features, are recorded. In addition to these measurements, cells are often analyzed in a number of fluorescent channels or with a spectral analyzer. These detection modes are used to distinguish biomarker profiles and other biological features between different cell populations.

Most synthetic or polymer products used in cellular analysis are made of a plastic material such as polystyrene (latex), an opaque polymer that generally has a fixed forward and side scatter profile based on the diameter of the particle. In addition, polystyrene has high autofluorescence in important detection channels, which leads to background fluorescent signal, even in the absence of a fluorophore or relevant biomarker. In other cases, polystyrene has autofluorescence that is much lower than cellular material, leading to inaccurate compensation and spectral unmixing. Overall, the inherent autofluorescence of polystyrene makes it unsuitable for fluorescence calibration and compensation in many cases. Specifically, rare or low-expression biomarkers cannot be distinguished properly from polystyrene particles, precluding their use as controls/standards. In addition, autofluorescence from polystyrene particles can lead to spurious fluorescence resonance energy transfer (FRET), which contributes to poor signal-to-noise with dyes that rely on FRET for functionality (e.g., tandem dyes). Autofluorescence interference caused by polystyrene is exacerbated in spectral analysis, which resolves the full spectral profile of a given target vs. an isolated fluorescence channel. Together, these inherent limitations of polystyrene make it suboptimal as a substrate when performing calibration and compensation with a range of fluorochromes, especially those which display excitation or emission profiles in the violet and ultraviolet range.

Several critical cytometric instrument set up procedures rely on the ability of a calibration particle to mimic a cell as closely as possible. In cytometry, compensation is a mathematical correction of a signal overlap between the channels of the emission spectra of different fluorochromes. Compensation is critical when assaying diverse biochemical targets using multiple unique fluorophores, as it is important to distinguish a true signal response from "spillover" signal, or interference from a different fluorescent channel. In some known implementations, fluorescence compensation uses polystyrene-based controls to demonstrate the fluorescence resolution of a given panel of antibodies/fluorophores. Due to the autofluorescence of polystyrene, however, there are entire classes of fluorophores (e.g., tandem dyes, UV/violet-responsive dyes), many of which cannot be effectively compensated for existing bead-based polystyrene products. The autofluorescence and poor performance of polystyrene fundamentally limits the complexity and diversity of the fluorophores used during cellular analysis.

Therefore, there is a need for substrates that more closely mimic the autofluorescence of actual cells.

SUMMARY

In some embodiments, a method includes calibrating a cytometric device for analysis of a target cell, by inserting, into the cytometric device, a hydrogel particle. The hydrogel particle has at least one of an autofluorescent property or a spectral property that is substantially similar to the at least one of an autofluorescent property or a spectral property of the target cell. The method also includes measuring at least one property of the hydrogel particle using the cytometric device.

In some embodiments of the present disclosure, a composition comprises a hydrogel particle having an autofluorescence profile or a spectral profile that is more similar to a cell, as compared to an autofluorescence profile or a spectral profile of polystyrene (e.g., latex), as measured by a cytometric device.

In other embodiments, the present disclosure provides for methods of producing a hydrogel particle that has autofluorescent properties or spectral properties that are substantially similar to the corresponding autofluorescent properties or spectral properties of a target cell. The present disclosure also sets forth methods of producing a hydrogel particle that has pre-determined autofluorescent properties and/or spectral properties. The present disclosure also sets forth a method of calibrating a cytometric device for analysis of a target cell, the method comprising a) inserting into the cytometric device a hydrogel particle having autofluorescent properties and/or spectral properties that are substantially similar to the corresponding autofluorescent properties and/or spectral properties of the target cell; and b) measuring the fluorescent properties and/or or spectral properties of the hydrogel particle using the cytometric device, thereby calibrating the cytometric device for analysis of the target cell.

In some embodiments, a method includes calculating a compensation value for a cytometric measurement of a target cell and modifying the cytometric measurement of the target cell based on the compensation value. The calculating the compensation value for the cytometric measurement of the target cell includes inserting, into the cytometric device and at a first time, a first hydrogel particle. The first hydrogel particle has at least one of a background fluorescent property or a spectral property that is substantially similar to the at least one of a background fluorescent property or a spectral property of the target cell. At least one property of the first hydrogel particle is measured using the cytometric device. The calculating also includes inserting, into the cytometric device and at a second time different from the first time, a second hydrogel particle, and measuring at least one property of the second hydrogel particle using the cytometric device. The calculating also includes comparing the measured at least one property of the first hydrogel particle and the measured at least one property of the second hydrogel particle to determine the compensation value.

BRIEF DESCRIPTION OF THE FIGURES

FIGS. 11A-11D are bar graphs showing a comparison between cell staining, hydrogel compensation beads, and known (polystyrene-based) products, according to some embodiments.

FIG. 12 is a chart comparing the autofluorescences of polystyrene and a cellular control with autofluorescence of example hydrogels of the present disclosure with various compositions and properties, according to some embodiments.

DETAILED DESCRIPTION

Several known calibration measurements for flow cytometers, such as inter-laser delay, fluorescence response, sort timing, and fluorescence compensation, use polystyrene beads. These calibration measurements can be crucial for the accurate performance of the cytometer and for any downstream analysis or sorting of cell populations. Although polystyrene is robust and low cost in comparison to using cellular controls, it exhibits inherently different optical and fluorescent behaviors, as compared to a cell. As a result, polystyrene beads represent a poor surrogate for cellular controls in all but the most rudimentary calibration processes.

To overcome the limitations of polystyrene, cells are sometimes used during instrument set up and calibration, however such approaches suffer from batch to batch variability, high cost, poor shelf-life, and biohazardous shipping/handling limitations. Variation in cellular size and differences between user-prepared cells make them unsuitable for certain instrument calibration controls. In addition, cellular control material is often challenging to source when examining rare diseases.

The particles of the present disclosure display cell-like autofluorescence and spectral profile, in contrast to polystyrene, allowing for more sensitive calibration of instrumentation, better fluorescence compensation, and better overall experimental data resolution. The particles are also synthetically manufactured, allowing for high batch to batch precision without any of the drawbacks of using cellular controls.

Figure 1A:
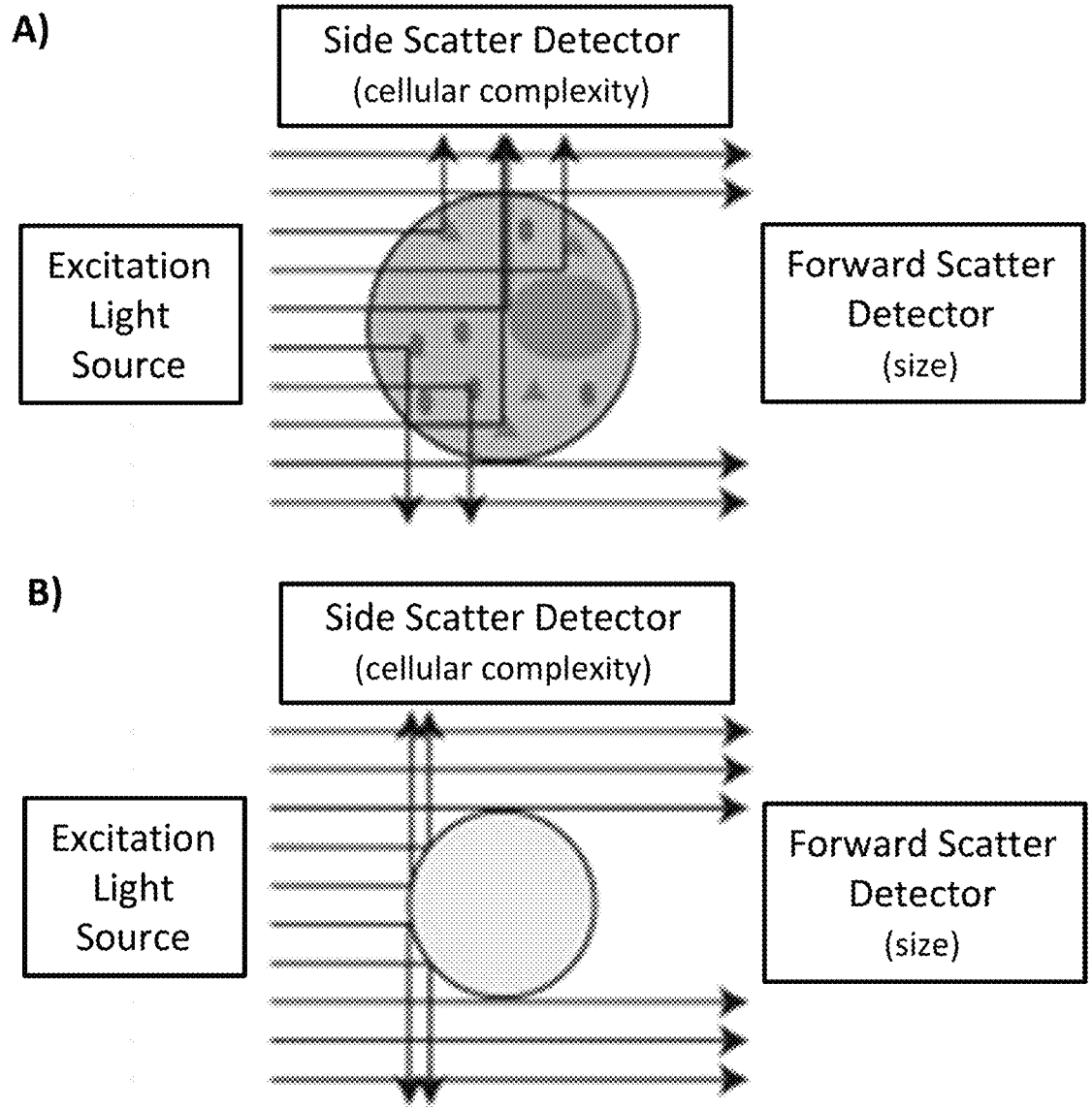
FIG. 1A illustrates example optical properties of (A) hydrogel particles of the present disclosure, (B) polystyrene bead, according to some embodiments.
Figure 1B:
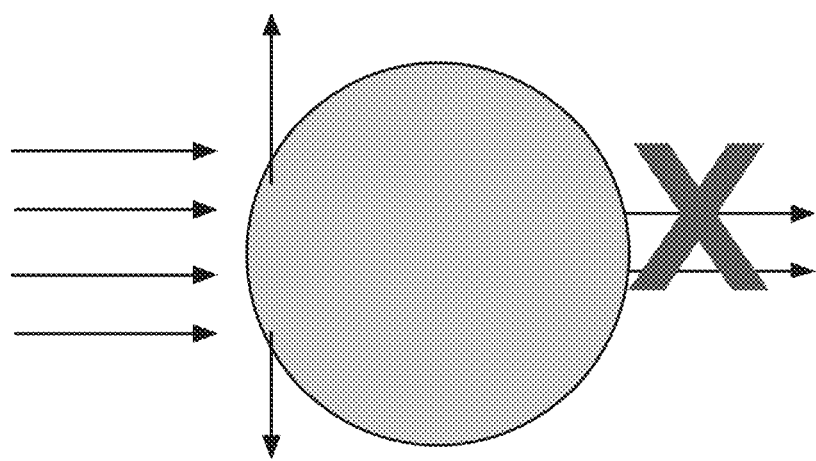
FIG. 1B illustrates optical properties of polystyrene beads, in contrast to the optical properties of the hydrogel particles of FIG. 1A(A).
Figure 2:
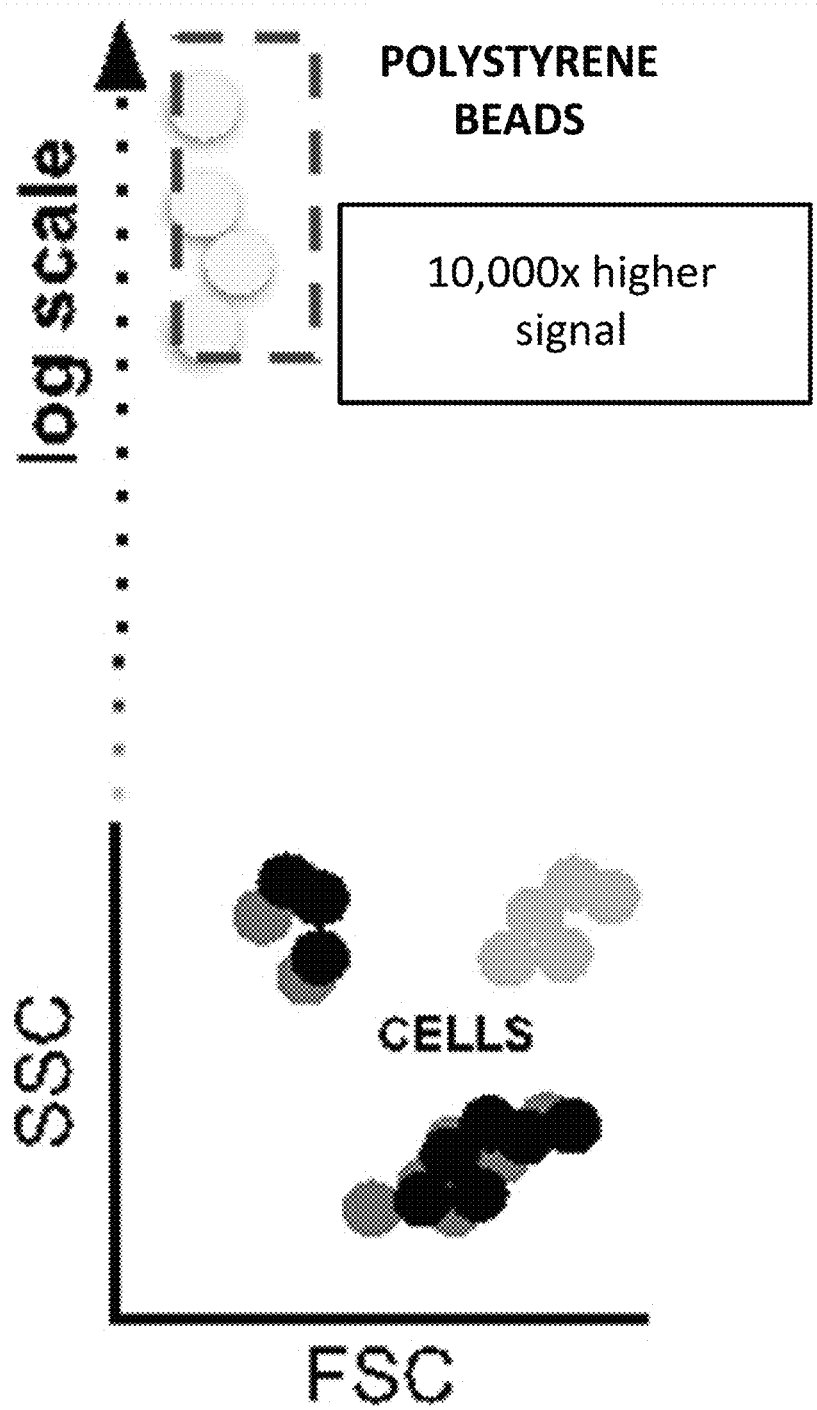
FIG. 2 depicts differences between scatter profiles of polystyrene and actual/target cells or hydrogel particles of the present disclosure, according to some embodiments.

As shown in FIGS. 1A-1B and 2, polystyrene particles are fundamentally limited with regard to the optical properties they can possess, such as forward and side scattering. This is largely due to the fact that they are opaque, in contrast to cells, so side scattering is a direct function of the size of a particle, as opposed to internal cellular complexity. For example, FIG. 1A(A) shows example optical properties of engineered hydrogel particles of the present disclosure, whereby light from an excitation light source can interact with the internal structure of the engineered hydrogel particles to generate side scatter information about that internal structure. FIGS. 1A(B) and 1B, by contrast, shows example optical properties of polystyrene beads, whereby light from an excitation light source does not interact with the internal structure of the polystyrene beads, and thus, the resulting side scatter information is limited. Moreover, as shown in FIG. 2, polystyrene beads have 3-4 orders of magnitude difference in side scatter profile, as compared to actual cells (e.g., target biological cells). In addition, polystyrene has high autofluorescence in many channels, even in the absence of fluorophores, which leads to poor detector resolution (see, e.g., FIGS. 7A-7C, discussed further below). In other instances, polystyrene has low autofluorescence, when compared to cellular material, leading to inaccurate staining index calculations, compensation or spectral unmixing. This phenomenon makes it exceedingly difficult or impossible to accurately measure rare or poorly-expressed biomarkers in samples. This also leads to poor compensation performance in channels where polystyrene autofluoresces. Due to these limitations of polystyrene, users must often rely on purified cell lines to calibrate fluorescent intensity, fluorescence compensation, inter-laser delay, sort delays, size and cellular complexity for immunophenotyping experiments. This is a lengthy and labor-intensive process that increases the cost of flow cytometry validation and research pipelines significantly. More importantly, these calibration cell lines introduce biological variation, causing disparities in the interpretation of immunophenotyping data.

To utilize multiple fluorophores for a given biomarker phenotyping experiment, the fluorophores should be distinguishable on the cytometric instrument. The fluorescent profile of a given antibody, when bound to a cell containing a cognate biomarker/antigen, can be used to compare to other antibody-fluorophore combinations used in the same "panel" of reagents. Due to the challenges of using cells for fluorescence compensation, polystyrene beads are often used as a proxy during fluorescence compensation set up. The background autofluorescence of polystyrene, however, leads to poor detector resolution, inaccurate compensation matrix calculations, background autofluorescence, and a poor lower limit of detection threshold.

Embodiments of the present disclosure provide for compositions comprising a hydrogel particle having background fluorescent properties (e.g., autofluorescence) that are substantially similar to the background fluorescent properties of a target cell (e.g., a human cell), and that overcome the various disadvantages of polystyrene discussed above. Hydrogel particles described herein can have background spectral profiles that are substantially similar to the background spectral profile of a target cell. The inventors have unexpectedly discovered that fluorescent properties of a hydrogel particle can be independently modulated by altering the composition of the hydrogel particle. In addition, the authors have found that the background fluorescent properties of hydrogel particles can be modulated without impacting the baseline optical properties of the particle (i.e., autofluorescence can be modulated independently of forward scattering (FSC) and side scattering (SSC)). This property allows the hydrogels to precisely mimic both the optical and autofluorescent properties of a target cell as measured by a cytometric device.

The present disclosure also provides for methods of producing a hydrogel particle, wherein the hydrogel particle has fluorescent properties substantially similar to the fluorescent properties of a target cell. The present disclosure also provides for methods of producing a hydrogel particle, wherein the hydrogel particle has pre-determined optical properties or fluorescent properties. Also provided for is a method of calibrating a cytometric device for analysis of a target cell, the method comprising a) inserting into the device a hydrogel particle having fluorescent properties substantially similar to the fluorescent properties of the target cell; b) measuring the fluorescent properties of the hydrogel particle using the cytometric device, thereby calibrating the cytometric device for analysis of the target cell. Known cytometric devices include commercially available devices for performing flow cytometry, fluorescence-activated cell sorting (FACS), hematology and high-content imaging.

Hydrogels

Hydrogel particles of the present disclosure comprise a hydrogel. A hydrogel is a material comprising a macromolecular three-dimensional network that allows it to swell when in the presence of water, and to shrink in the absence of (or by reduction of the amount of) water, but not dissolve in water. The swelling, i.e., the absorption of water, is a consequence of the presence of hydrophilic functional groups attached to or dispersed within the macromolecular network. Crosslinks between adjacent macromolecules result in the aqueous insolubility of these hydrogels. The cross-links may be due to chemical (e.g., covalent) or physical (e.g., Van Der Waal forces, hydrogen-bonding, ionic forces, etc.) bonds. While some in the polymer industry may refer to one or more of the macromolecular materials described herein as a "xerogel" in the dry state and a "hydrogel" in the hydrated state, for purposes of the present disclosure, the term "hydrogel" refers to the macromolecular material whether dehydrated or hydrated. A characteristic of a hydrogel that is of particular value is that the material retains its general shape, whether it is dehydrated or hydrated. Thus, if the hydrogel has an approximately spherical shape in the dehydrated condition, it will be spherical in the hydrated condition.

Disclosed hydrogels of the present disclosure, according to some embodiments, can comprise, by way of example, greater than about 30% water, greater than about 40% water, greater than about 50% water, greater than about 55% water, greater than about 60% water, greater than about 65% water, greater than about 70% water, greater than about 75% water, greater than about 80%, water or greater than about 85% water.

Synthetically prepared hydrogels can be prepared by polymerizing a monomeric material to form a backbone and cross-linking the backbone with a crosslinking agent. Common hydrogel monomers include the following: lactic acid, glycolic acid, acrylic acid, 1-hydroxyethyl methacrylate, ethyl methacrylate, propylene glycol methacrylate, acrylamide, N-vinylpyrrolidone, methyl methacrylate, glycidyl methacrylate, glycol methacrylate, ethylene glycol, fumaric acid, and the like. Common cross linking agents include tetraethylene glycol dimethacrylate and N,N'-15 methylenebisacrylamide. In some embodiments, a hydrogel particle of the disclosure is produced by the polymerization of acrylamide.

In some embodiments, a hydrogel comprises a mixture of at least one monofunctional monomer and at least one bifunctional monomer.

A monofunctional monomer can be a monofunctional acrylic monomer. Non-limiting examples of monofunctional acrylic monomers are acrylamide; methacrylamide; N-alkylacrylamides such as N-ethylacrylamide, N-isopropylacrylamide or N-tert-butylacrylamide; N-alkylmethacrylamides such as N-ethylmethacrylamide or N-isopropylmethacrylamide; N,N-dialkylacrylamides such as N,N-dimethylacrylamide and N,N-diethyl-acrylamide; N-[(dialkylamino)alkyl]acrylamides such as N-[3dimethylamino)propyl]acrylamide or N-[3-(diethylamino)propyl]acrylamide; N-[(dialkylamino)alkyl]methacrylamides such as N-[3-dimethylamino)propyl]methacrylamide or N-[3-(diethylamino) propyl]methacrylamide; (dialkylamino)alkyl acrylates such as 2-(dimethylamino)ethyl acrylate, 2-(dimethylamino)propyl acrylate, or 2-(diethylamino)ethyl acrylates; and (dialkylamino)alkyl methacrylates such as 2-(dimethylamino) ethyl methacrylate.

A bifunctional monomer is any monomer that can polymerize with a monofunctional monomer of the disclosure to form a hydrogel as described herein that further contains a second functional group that can participate in a second reaction, e.g., conjugation of a fluorophore.

In some embodiments, a bifunctional monomer is selected from the group consisting of: allyl alcohol, allyl isothiocyanate, allyl chloride, and allyl maleimide.

A bifunctional monomer can be a bifunctional acrylic monomer. Non-limiting examples of bifunctional acrylic monomers are N,N'-methylenebisacrylamide, N,N'-methylenebismethacrylamide, N,N'-ethylenebisacrylamide, N,N'-ethylenebis-methacrylamide, N,N'propylenebisacrylamide and N,N'-(1,2-dihydroxyethylene)bisacrylamide.

Higher-order branched chain and linear co-monomers can be substituted in the polymer mix to adjust the refractive index while maintaining polymer density, as described in U.S. Pat. No. 6,657,030, the contents of which are incorporated herein by reference in their entirety.

In some embodiments, a hydrogel comprises a molecule that modulates the optical properties of the hydrogel. Molecules capable of altering optical properties of a hydrogel are discussed further below.

Naturally occurring hydrogels useful in this invention include various polysaccharides available from natural sources such as plants, algae, fungi, yeasts, marine invertebrates and arthropods. Non-limiting examples include agarose, dextrans, chitin, cellulose-based compounds, starch, derivatized starch, and the like. These generally will have repeating glucose units as a major portion of the polysaccharide backbone.

Polymerization of a hydrogel can be initiated by a persulfate. The persulfate can be any water-soluble persulfate. Non-limiting examples of water soluble persulfates are ammonium persulfate and alkali metal persulfates. Alkali metals include lithium, sodium and potassium. In some preferred embodiments, the persulfate is ammonium persulfate or potassium persulfate, more preferably, it is ammonium persulfate.

Polymerization of a hydrogel can be accelerated by an accelerant. The accelerant can be a tertiary amine. The tertiary amine can be any water-soluble tertiary amine. Preferably, the tertiary amine is N,N,N',N'tetramethylethylenediamine or 3-dimethylamino)propionitrile, more preferably it is N,N,N',N'tetramethylethylenediamine (TEMED).

Hydrogel Particles

Figure 5:
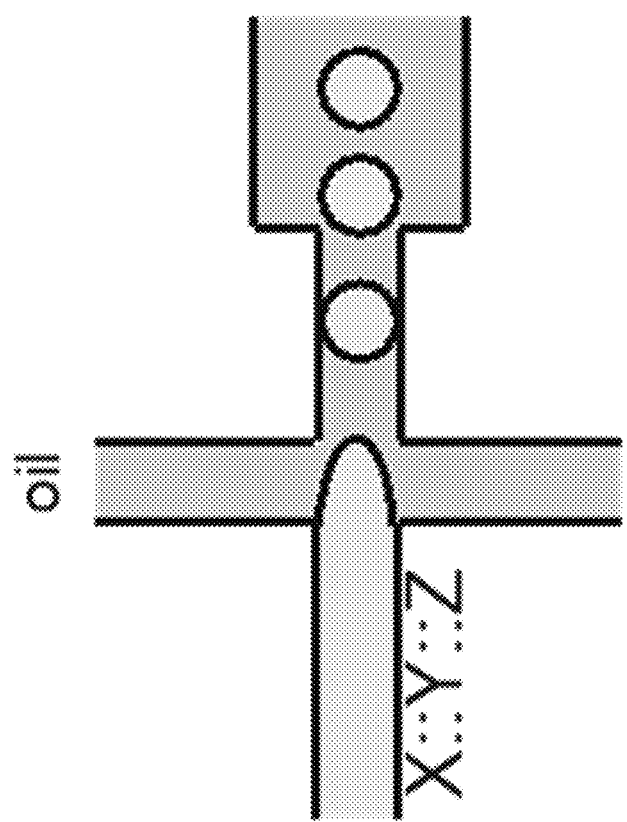
FIG. 5 illustrates an example method of producing hydrogel particles, according to some embodiments.

In one aspect, a hydrogel particle of the disclosure comprises a hydrogel and is produced by polymerizing a droplet (see FIG. 5). Microfluidic methods of producing a plurality of droplets, including fluidic and rigidified droplets, are known, and described in US Patent Application Publication No. 2011/0218123 and U.S. Pat. No. 7,294,503, the entire contents of each of which are incorporated herein by reference in their entireties. Such methods provide for a plurality of droplets containing a first fluid and being substantially surrounded by a second fluid, where the first fluid and the second fluid are substantially immiscible (e.g., droplets containing an aqueous-based liquid being substantially surrounded by an oil based liquid). In another form, a hydrogel particle is produced via precipitation or chemical polymerization. In another form, a hydrogel particle is produced via membrane emulsification. In another form, a hydrogel particle is formed via piezoelectric dispersion.

A plurality of fluidic droplets (e.g., prepared using a microfluidic device) may be polydisperse (e.g., having a range of different sizes), or in some cases, the fluidic droplets may be monodisperse or substantially monodisperse, e.g., having a homogenous distribution of diameters, for instance, such that no more than about 10%, about 5%, about 3%, about 1%, about 0.03%, or about 0.01% of the droplets have an average diameter greater than about 10%, about 5%, about 3%, about 1%, about 0.03%, or about 0.01% of the average diameter. The average diameter of a population of droplets, as used herein, refers to the arithmetic average of the diameters of the droplets.

Accordingly, the disclosure provides population of hydrogel particles comprising a plurality of hydrogel particles, wherein the population of hydrogel particles is substantially monodisperse.

The term microfluidic refers to a device, apparatus or system including at least one fluid channel having a cross-sectional dimension of less than 1 mm, and a ratio of length to largest cross-sectional dimension perpendicular to the channel of at least about 3:1. A microfluidic device comprising a microfluidic channel is especially well suited to preparing a plurality of monodisperse droplets.

Non-limiting examples of microfluidic systems that may be used with the present invention include those disclosed in U.S. Patent Application Publication No. 2006/0163385 ("Forming and Control of Fluidic Species"), U.S. Patent Application Publication No. 2005/0172476 ("Method and Apparatus for Fluid Dispersion"), U.S. Patent Application Publication No. 2007/000342 ("Electronic Control of Fluidic Species"), International Patent Application Publication No. WO 2006/096571 ("Method and Apparatus for Forming Multiple Emulsions"), U.S. Patent Application Publication No. 2007/0054119 ("Systems and Methods of Forming Particles"), International Patent Application Publication No. WO 2008/121342 ("Emulsions and Techniques for Formation"), and International Patent Application Publication No. WO 2006/078841 ("Systems and Methods for Forming Fluidic Droplets Encapsulated in Particles Such as Colloidal Particles"), the entire contents of each of which are incorporated herein by reference in their entireties.

Droplet size is related to microfluidic channel size. The microfluidic channel may be of any size, for example, having a largest dimension perpendicular to fluid flow of less than about 5 mm or 2 mm, or less than about 1 mm, or less than about 500 µm, less than about 200 µm, less than about 100 µm, less than about 60 µm, less than about 50 µm, less than about 40 µm, less than about 30 µm, less than about 25 µm, less than about 10 µm, less than about 3 µm, less than about 1 µm, less than about 300 nm, less than about 100 nm, less than about 30 nm, or less than about 10 nm.

Droplet size can be tuned by adjusting the relative flow rates. In some embodiments, drop diameters are equivalent to the width of the channel, or within about 10%, 15%, 20%, 30%, 40%, 50%, 60%, 70%, 80%, 90%, or 100% the width of the channel.

The dimensions of a hydrogel particle of the disclosure are substantially similar to the droplet from which it was formed. Therefore, in some embodiments, a hydrogel particle has a diameter of less than about 1 µm, 2, 5, 10, 15, 20, 25, 30, 35, 40, 45, 50, 60, 70, 80, 90, 100, 120, 150, 200, 250, 300, 350, 400, 450, 500, 600, 800, or less than 1000 µm in diameter. In some embodiments, a hydrogel particle has a diameter of more than about 1 µm, 2, 5, 10, 15, 20, 25, 30, 35, 40, 45, 50, 60, 70, 80, 90, 100, 120, 150, 200, 250, 300, 350, 400, 450, 500, 600, 800, or greater than 1000 µm in diameter. In typical embodiments, a hydrogel particle has a diameter in the range of 5 μm to 100 μm.

In some embodiments, a hydrogel particle of the disclosure is spherical in shape.

In some embodiments, a hydrogel particle of the disclosure has material modulus properties (e.g., elasticity) more closely resembling that of a target cell as compared to a polystyrene bead of the same diameter.

In some embodiments, a hydrogel particle of the disclosure does not comprise agarose.

Optical Properties

Passive Optical Properties and Non-Passive Optical Properties (e.g., Fluorescent Properties)

The three primary modes of deconvolution for flow cytometry are the two passive optical properties of a particle (forward scattering, FSC, corresponding to the refractive index, or RI; and side scattering, SSC) and fluorescence, which is a non-passive optical property (i.e., a property that is imparted by a molecule that is not a component of the base polymer, such as a fluorophore, fluorochrome, or quantum dot), and which is representative of biomarkers present on the surface of a given cell type that are typically measured using antibodies with conjugated fluorophores. Therefore, compositions that allow hydrogel particles of the disclosure to mimic specific cell types with respect to these three modes are useful for providing synthetic, robust calibrants for flow cytometry.

In some embodiments, the refractive index (RI) of a disclosed hydrogel particle is greater than about 1.10, greater than about 1.15, greater than about 1.20, greater than about 1.25, greater than about 1.30, greater than about 1.35, greater than about 1.40, greater than about 1.45, greater than about 1.50, greater than about 1.55, greater than about 1.60, greater than about 1.65, greater than about 1.70, greater than about 1.75, greater than about 1.80, greater than about 1.85, greater than about 1.90, greater than about 1.95, greater than about 2.00, greater than about 2.10, greater than about 2.20, greater than about 2.30, greater than about 2.40, greater than about 2.50, greater than about 2.60, greater than about 2.70, greater than about 2.80, or greater than about 2.90.

In some embodiments, the refractive index (RI) of a disclosed hydrogel particle is less than about 1.10, less than about 1.15, less than about 1.20, less than about 1.25, less than about 1.30, less than about 1.35, less than about 1.40, less than about 1.45, less than about 1.50, less than about 1.55, less than about 1.60, less than about 1.65, less than about 1.70, less than about 1.75, less than about 1.80, less than about 1.85, less than about 1.90, less than about 1.95, less than about 2.00, less than about 2.10, less than about 2.20, less than about 2.30, less than about 2.40, less than about 2.50, less than about 2.60, less than about 2.70, less than about 2.80, or less than about 2.90.

The SSC of a disclosed hydrogel particle is most meaningfully measured in comparison to that of target cell. In some embodiments, a disclosed hydrogel particle has an SSC within 30%, within 25%, within 20%, within 15%, within 10%, within 5%, or within 1% that of a target cell, as measured by a cytometric device.

The FSC of a disclosed hydrogel particle is most meaningfully measured in comparison to that of target cell. In some embodiments, a disclosed hydrogel particle has an FSC within 30%, within 25%, within 20%, within 15%, within 10%, within 5%, or within 1% that of a target cell, as measured by a cytometric device.

FSC can be tuned for a hydrogel by incorporating a high-refractive index molecule in the hydrogel. Preferred high-refractive index molecules include colloidal silica, alkyl acrylate and alkyl methacrylate. Thus in some embodiments, a hydrogel particle of the disclosure comprises alkyl acrylate and/or alkyl methacrylate.

Alkyl acrylates or Alkyl methacrylates can contain 1 to 18, 1 to 8, or 2 to 8, carbon atoms in the alkyl group, such as methyl, ethyl, n-propyl, isopropyl, n-butyl, isobutyl or tert-butyl, 2-ethylhexyl, heptyl or octyl groups. The alkyl group may be branched or linear.

High-refractive index molecules can also include vinylarenes such as styrene and methylstyrene, optionally substituted on the aromatic ring with an alkyl group, such as methyl, ethyl or tert-butyl, or with a halogen, such as chlorostyrene.

In some embodiments, FSC is modulated by adjusting the water content present during hydrogel formation.

FSC is related to particle volume, and thus can be modulated by altering particle diameter, as described herein.

SSC can be engineered by encapsulating nanoparticles within hydrogels to mimic organelles in a target cell. In some embodiments, a hydrogel particle of the disclosure comprises one or more types of nanoparticles selected from the group consisting of: polymethyl methacrylate (PMMA) nanoparticles, polystyrene (PS) nanoparticles, and silica nanoparticles.

Functionalization of Hydrogel Particles

Hydrogel particles can be functionalized, allowing them to mimic optical and fluorescent properties of labeled cells. In some embodiments, a hydrogel particle comprises a bifunctional monomer, and functionalization of the hydrogel particle occurs via the bifunctional monomer. In typical embodiments, a functionalized hydrogel particle comprises a free amine group.

A hydrogel particle can be functionalized with any fluorescent dye of fluorochrome known in the art, including fluorescent dyes listed in The MolecularProbes® Handbook—A Guide to Fluorescent Probes and Labeling Technologies, incorporated herein by reference in its entirety. Functionalization can be mediated by a compound comprising a free amine group, e.g. allylamine, which can be incorporated into a hydrogel particle during the formation process.

Non-limiting examples of known fluorescent dyes include: 6-carboxy-4', 5'-dichloro-2',7'-dimethoxyfluorescein succinimidylester; 5-(and 6)-carboxycosin; 5-carboxyfluorescein; 6-carboxyfluorescein; 5-(and 6)-carboxyfluorescein; 5-carboxyfluorescein-bis-(5-carboxymethoxy-2-nitrobenzyl)ether-alanine-carboxamide, or succinimidyl ester; 5-carboxyfluoresceinsuccinimidyl ester; 6-carboxyfluorescein succinimidyl ester; 5-(and 6)-carboxyfluorescein succinimidyl ester; 5-(4,6-dichlorotriazinyl) aminofluorescein; 2',7'-difluorofluorescein; cosin-5-isothiocyanate; erythrosin5-isothiocyanate; 6-(fluorescein-5-carboxamido)hexanoic acid or succinimidyl ester; 6-(fluorescein-5-(and 6)-carboxamido)hexanoic acid or succinimidylester; fluorescein-5-EX succinimidyl ester; fluorescein-5-isothiocyanate; fluorescein-6-isothiocyanate; OregonGreen® 488 carboxylic acid, or succinimidyl ester; Oregon Green® 488isothiocyanate; Oregon Green® 488-X succinimidyl ester; Oregon Green®500 carboxylic acid; Oregon Green® 500 carboxylic acid, succinimidylester or triethylammonium salt; Oregon Green® 514 carboxylic acid; Oregon Green® 514 carboxylic acid or succinimidyl ester; RhodamineGreen™ carboxylic acid, succinimidyl ester or hydrochloride; Rhodamine Green™ carboxylic acid, trifluoroacetamide or succinimidylester; Rhodamine Green™-X succinimidyl ester or hydrochloride; Rhodol-Green™ carboxylic acid, N,0-bis-(trifluoroacetyl) or succinimidylester; bis-(4-carboxypiperidinyl) sulfonerhodamine or di(succinimidylester); 5-(and 6)carboxynaphtho fluorescein, 5-(and 6)carboxynaphthofluorescein succinimidyl ester; 5-carboxyrhodamine 6G hydrochloride; 6-carboxyrhodamine 6Ghydrochloride, 5-carboxyrhodamine 6G succinimidyl ester; 6-carboxyrhodamine 6G succinimidyl ester; 5-(and 6)-carboxyrhodamine6G succinimidyl ester; 5-carboxy-2',4',5',7'-tetrabromosulfonefluorescein succinimidyl ester or bis-(diisopropylethylammonium) salt; 5-carboxytetramethylrhodamine; 6-carboxytetramethylrhodamine; 5-(and 6)-carboxytetramethylrhodamine; 5-carboxytetramethylrhodamine succinimidyl ester; 6-carboxytetramethylrhodamine succinimidyl ester; 5-(and 6)-carboxytetramethylrhodamine succinimidyl ester; 6-carboxy-X-rhodamine; 5-carboxy-X-rhodamine succinimidyl ester; 6-carboxy-Xrhodamine succinimidyl ester; 5-(and 6)-carboxy-Xrhodaminesuccinimidyl ester; 5-carboxy-X-rhodamine triethylammonium salt; Lissamine™ rhodamine B sulfonyl chloride; malachite green; isothiocyanate; NANOGOLD® mono(sulfosuccinimidyl ester); QSY® 21carboxylic acid or succinimidyl ester; QSY® 7 carboxylic acid or succinimidyl ester; Rhodamine Red™-X succinimidyl ester; 6-(tetramethylrhodamine-5-(and 6)-carboxamido)hexanoic acid; succinimidyl ester; tetramethylrhodamine-5-isothiocyanate; tetramethylrhodamine-6-isothiocyanate; tetramethylrhodamine-5-(and 6)-isothiocyanate; Texas Red® sulfonyl; Texas Red® sulfonyl chloride; Texas Red®-X STP ester or sodium salt; Texas Red®-X succinimidyl ester; Texas Red®-X succinimidyl ester; and X-rhodamine-5-(and 6)-isothiocyanate.

Other examples of fluorescent dyes include BODIPY® dyes commercially available from Invitrogen, including, but not limited to BODIPY® FL; BODIPY® TMR STP ester; BODIPY® TR-X STP ester; BODIPY® 630/650-X STPester; BODIPY® 650/665-X STP ester; 6-dibromo-4,4-difluoro-5,7-dimethyl-4-bora-3a,4a-diaza-s-indacene-3-propionic acid succinimidyl ester; 4,4-difluoro-4-bora-3a,4a-diaza-s-indacene-3,5-dipropionic acid; 4,4-difluoro-5,7-dimethyl-4-bora-3a,4a-diaza-s-indacene-3-pentanoicacid; 4,4-difluoro-5,7-dimethyl-4-bora3a,4a-diaza-s-indacene-3-pentanoicacid succinimidyl ester; 4,4-difluoro-5,7-dimethyl-4-bora-3a,4a-diaza-s-indacene-3propionicacid; 4,4-difluoro-5,7-dimethyl-4-bora-3a,4adiaza-s-indacene-3-propionicacid succinimidyl ester; 4,4difluoro-5,7-dimethyl-4-bora-3a,4a-diaza-s-indacene-3propionic acid; sulfosuccinimidyl ester or sodium salt; 6-((4,4-difluoro-5,7-dimethyl-4-bora-3a,4a-diaza-s-indacene-3propionyl)amino) hexanoicacid; 6-((4,4-difluoro-5,7-dimethyl-4-bora-3a,4a-diaza-s-indacene-3-propionyl)amino)hexanoic acid or succinimidyl ester; N-(4,4-difluoro5,7-dimethyl-4-bora-3a, 4a-diaza-s-indacene-3-propionyl)cysteic acid, succinimidyl ester or triethylammonium salt; 6-4,4-difluoro-1,3-dimethyl-5-(4-methoxyphenyl)-4-bora3a, 4a4,4-difluoro-5,7-diphenyl-4-bora-3a,4a-diaza-s-indacene-3-propionicacid; 4,4-difluoro-5,7-diphenyl-4-bora3a,4a-diaza-s-indacene-3-propionicacid succinimidyl ester; 4,4-difluoro-5-phenyl-4-bora-3a,4a-diaza-s-indacene-3-propionic acid; succinimidyl ester; 6-((4,4-difluoro-5-phenyl-4bora-3a,4a-diaza-s-indacene-3-propionyl)amino)hexanoicacid or succinimidyl ester; 4,4-difluoro-5-(4-phenyl-1,3butadienyl)-4-bora-3a, 4a-diaza-s-indacene-3-propionicacid succinimidyl ester; 4,4-difluoro-5-(2-pyrrolyl)-4-bora-3a,4a-diaza-s-indacene-3-propionic acid succinimidyl ester; 6-(((4,4-difluoro-5-(2-pyrrolyl)-4-bora-3a,4a-diaza-s-indacene-3-yl)styryloxy) acetyl)aminohexanoicacid or succinimidyl ester; 4,4-difluoro-5-styryl-4-bora-3a,4a-diaza-s-indacene-3-propionic acid; 4,4-difluoro-5-styryl-4-bora-3a, 4a-diaza-s-indacene-3-propionic acid; succinimidyl ester; 4,4-difluoro-1,3,5,7-tetramethyl-4-bora-3a,4a-diaza-s-indacene-8-propionicacid; 4,4-difluoro-1,3,5,7-tetramethyl-4bora-3a, 4a-diaza-s-indacene-8-propionicacid succinimidyl ester; 4,4-difluoro-5-(2-thienyl)-4-bora-3a,4a-diaza-s-indacene-3-propionicacid succinimidyl ester; 6-(((4-(4,4-difluoro-5-(2-thienyl)-4-bora-3a,4a-diazas-indacene-3-yl)phenoxy) acetyl)amino)hexanoic acid or succinimidyl ester; and 6-(((4,4-difluoro-5-(2-thienyl)-4-bora-3a,4a-diaza-s-indacene-3-yl)styryloxy)acetyl)aminohexanoicacid or succinimidyl ester.

Fluorescent dyes can also include for example, Alexa fluor dyes commercially available from Invitrogen, including but not limited to Alexa Fluor® 350 carboxylic acid; Alexa Fluor® 430 carboxylic acid; Alexa Fluor® 488 carboxylic acid; Alexa Fluor® 532 carboxylic acid; Alexa Fluor® 546 carboxylic acid; Alexa Fluor® 555 carboxylic acid; Alexa Fluor® 568 carboxylic acid; Alexa Fluor® 594 carboxylic acid; Alexa Fluor® 633 carboxylic acid; Alexa Fluor® 647 carboxylic acid; Alexa Fluor® 660 carboxylic acid; and Alexa Fluor® 680 carboxylic acid. Fluorescent dyes the present invention can also be, for example, cyanine dyes commercially available from Amersham-Pharmacia Biotech, including, but not limited to Cy3 NHS ester; Cy 5 NHS ester; Cy5.5 NHSester; and Cy7 NHS ester.

Tandem dyes, such as those containing PE-Cy5, or other combinations, can also be utilized effectively in this disclosure due to low autofluorescence. Typically, polystyrene autofluorescence will interfere with Fluorescence Resonance Energy Transfer (FRET) signals required to utilize tandem or polymeric dyes.

Target Cells

Hydrogel particles of the disclosure behave similarly to target cells in procedures such as staining and analysis by flow cytometry or FACS.

In some embodiments, a target cell is an immune cell. Non-limiting examples of immune cells include B lymphocytes, also called B cells, T lymphocytes, also called T cells, natural killer (NK) cells, lymphokine-activated killer (LAK) cells, monocytes, macrophages, neutrophils, granulocytes, mast cells, platelets, Langerhans cells, stem cells, dendritic cells, peripheral blood mononuclear cells, tumor infiltrating (TIL) cells, gene modified immune cells including hybridomas, drug modified immune cells, and derivatives, precursors or progenitors of any of the cell types listed herein.

In some embodiments, a target cell encompasses all cells of a particular class of cell with shared properties. For example, a target cell can be a lymphocyte, including NK cells, T cells, and B cells. A target cell can be an activated lymphocyte.

In some embodiments, a target cell is a primary cell, cultured cell, established cell, normal cell, transformed cell, infected cell, stably transfected cell, transiently transfected cell, proliferating cell, or terminally differentiated cells.

In one embodiment, a target cell is a primary neuronal cell. A variety of neurons can be target cells. As non-limiting examples, a target cell can be a primary neuron; established neuron; transformed neuron; stably transfected neuron; or motor or sensory neuron.

In other embodiments, a target cell is selected from the group consisting of: primary lymphocytes, monocytes, and granulocytes.

A target cell can be virtually any type of cell, including prokaryotic and eukaryotic cells.

Suitable prokaryotic target cells include, but are not limited to, bacteria such as *E. coli*, various *Bacillus* species, and the extremophile bacteria such as thermophiles.

Suitable eukaryotic target cells include, but are not limited to, fungi such as yeast and filamentous fungi, including species of *Saccharomyces, Aspergillus, Trichoderma*, and *Neurospora*; plant cells including those of corn, sorghum, tobacco, canola, soybean, cotton, tomato, potato, alfalfa, sunflower, etc.; and animal cells, including fish, birds and mammals. Suitable fish cells include, but are not limited to, those from species of salmon, trout, tilapia, tuna, carp, flounder, halibut, swordfish, cod and zebrafish. Suitable bird cells include, but are not limited to, those of chickens, ducks, quail, pheasants and turkeys, and other jungle foul or game birds. Suitable mammalian cells include, but are not limited to, cells from horses, cows, buffalo, deer, sheep, rabbits, rodents such as mice, rats, hamsters and guinea pigs, goats, pigs, primates, marine mammals including dolphins and whales, as well as cell lines, such as human cell lines of any tissue or stem cell type, and stem cells, including pluripotent and non-pluripotent, and non-human zygotes.

Suitable cells also include those cell types implicated in a wide variety of disease conditions, even while in a non-diseased state. Accordingly, suitable eukaryotic cell types include, but are not limited to, tumor cells of all types (e.g., melanoma, myeloid leukemia, carcinomas of the lung, breast, ovaries, colon, kidney, prostate, pancreas and testes), cardiomyocytes, dendritic cells, endothelial cells, epithelial cells, lymphocytes (T-cell and B cell), mast cells, eosinophils, vascular intimal cells, macrophages, natural killer cells, erythrocytes, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. In certain embodiments, the cells are primary disease state cells, such as primary tumor cells. Suitable cells also include known research cells, including, but not limited to, Jurkat T cells, NIH3T3 cells, CHO, COS, etc. See the ATCC cell line catalog, hereby expressly incorporated by reference.

In some embodiments, a target cell is a tumor microvesicle or tumor macrovesicle. Tumor microvesicles, also known as tumor-secreted microvesicles or tumor-secreted exosomes, can be found in circulating blood and may have immune-suppressive activities. Tumor microvesicles typically range in size from 30-200 nm in diameter. Larger tumor microvesicles may be referred to as tumor macrovesicles, and can range in size from 3-10 μm in diameter.

EXAMPLES

Example 1: Generation of Hydrogel Particles

Photomasks for UV lithography were sourced from CADart Services Inc. and were designed using AutoCad (AutoDesk, Inc.). SU-8 photo resist (Microchem, Inc.) was photo crosslinked on 4" silicon wafers using a collimated UV light source (OAI, Inc.) to create masters for microfluidic device fabrication. PDMS (polydimethylsiloxane, Sigma Aldrich, Inc.) was prepared and formed using standard published methods for soft lithography and microfluidic device fabrication (See, McDonald J C, et al., 2000, Electrophoresis 21:27-40).

Droplets were formed using flow-focusing geometry where two oil channels focus a central stream of aqueous monomer solution to break off droplets in a water-in-oil emulsion. A fluorocarbon-oil (Novec 7500 3M, Inc.) was used as the outer, continuous phase liquid for droplet formation. To stabilize droplets before polymerization, a surfactant was added at 0.5% w/w to the oil phase (ammonium carboxylate salt of Krytox 157 FSH, Dupont). To make the basic polyacrylamide gel particle, a central phase of an aqueous monomer solution containing N-acrylamide (1-20% w/v), a cross-linker (N,N'-bisacrylamide, 0.05-1% w/v), an accelerator, and ammonium persulfate (1% w/v) was used. An accelerator, (N,N,N',N'-tetramethylethylenediamine 2% vol %) was added to the oil-phase in order to trigger hydrogel particle polymerization after droplet formation.

Several co-monomers were added to the basic gel formulation to add functionality. In one example, aryl-acrylates were added to modulate the autofluorescent properties of the particle. In other examples, polystyrene nanoparticles were added, at low concentrations, to the hydrogel matrix to modulate the autofluorescence properties of the particle. Fluorescent properties were also modulated by adjusting the crosslinking density of the particle, by engineering the kinetics of crosslinking and curing processes (e.g., changing one of temperature, time, and/or concentration of one or more accelerants). Co-monomers, nanoparticulate additives, and crosslinking density of the basic gel formulation were modulated to impact the fluorescence and spectral properties of the particles to create a formulation model that mimics cell-like background optical response. Specifically, the types of chemical side groups present on various co-monomers incorporated into the gel matrix impacts the fluorescence and spectral properties of the particle, as does the concentration of the co-monomers, additives, and crosslinking density of the core polymer.

Stoichiometric multiplexing of the hydrogel particles was achieved by utilizing co-monomers containing chemically orthogonal side groups (amine, carboxyl, maleimide, epoxide, alkyne, etc.) for secondary labeling.

We formed droplets at an average rate of 5 kHz and collected them in the fluorocarbon oil phase. After completing polymerization at 50° C. for 30 minutes, we washed the resulting hydrogel particles from the oil into an aqueous solution.

Example 2: Multidimensional Tuning of Hydrogel Particle Optical Properties

Figure 3:
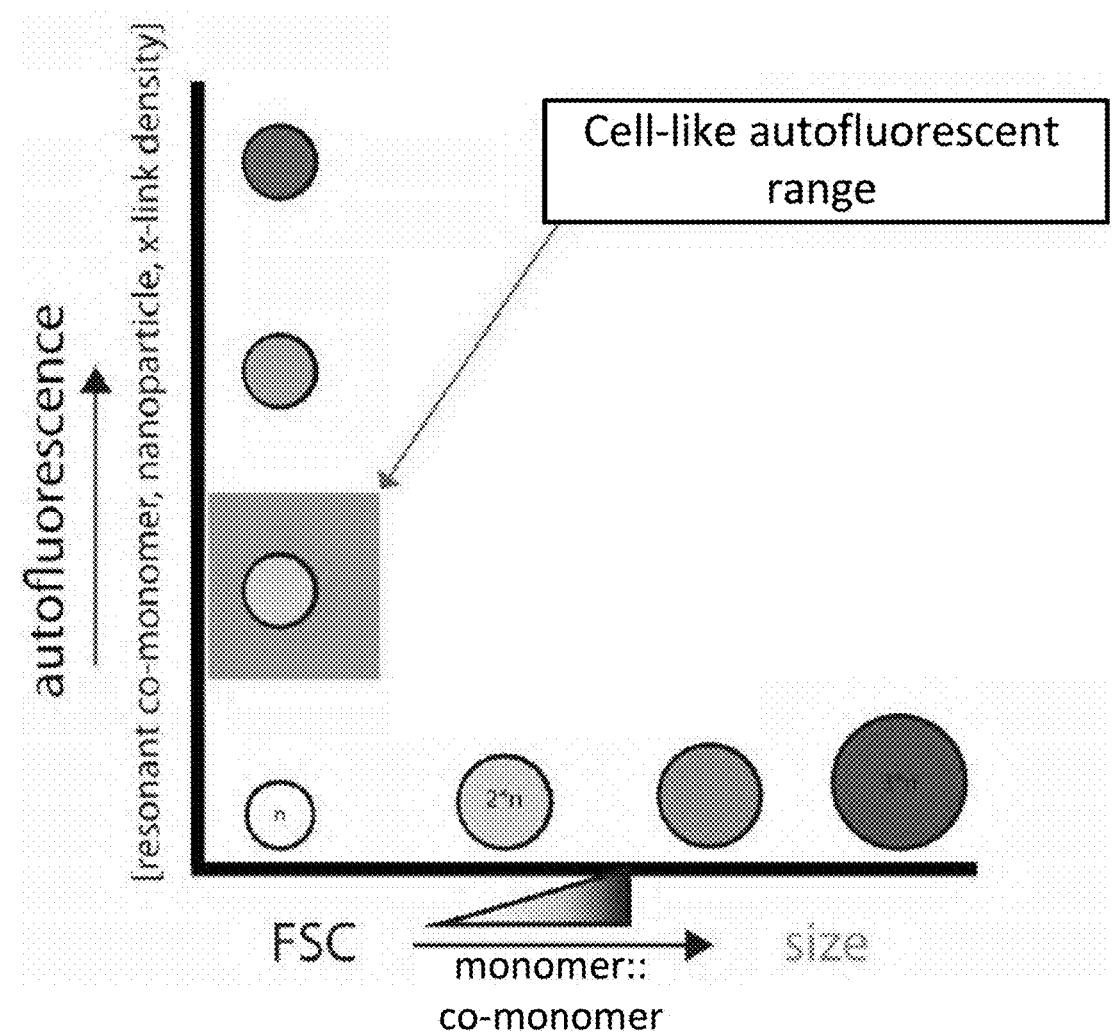
FIG. 3 illustrates how the autofluorescent or spectral properties of a hydrogel can be engineered to match the autofluorescence or spectral properties of a target cell population, according to some embodiments.
Figure 4:
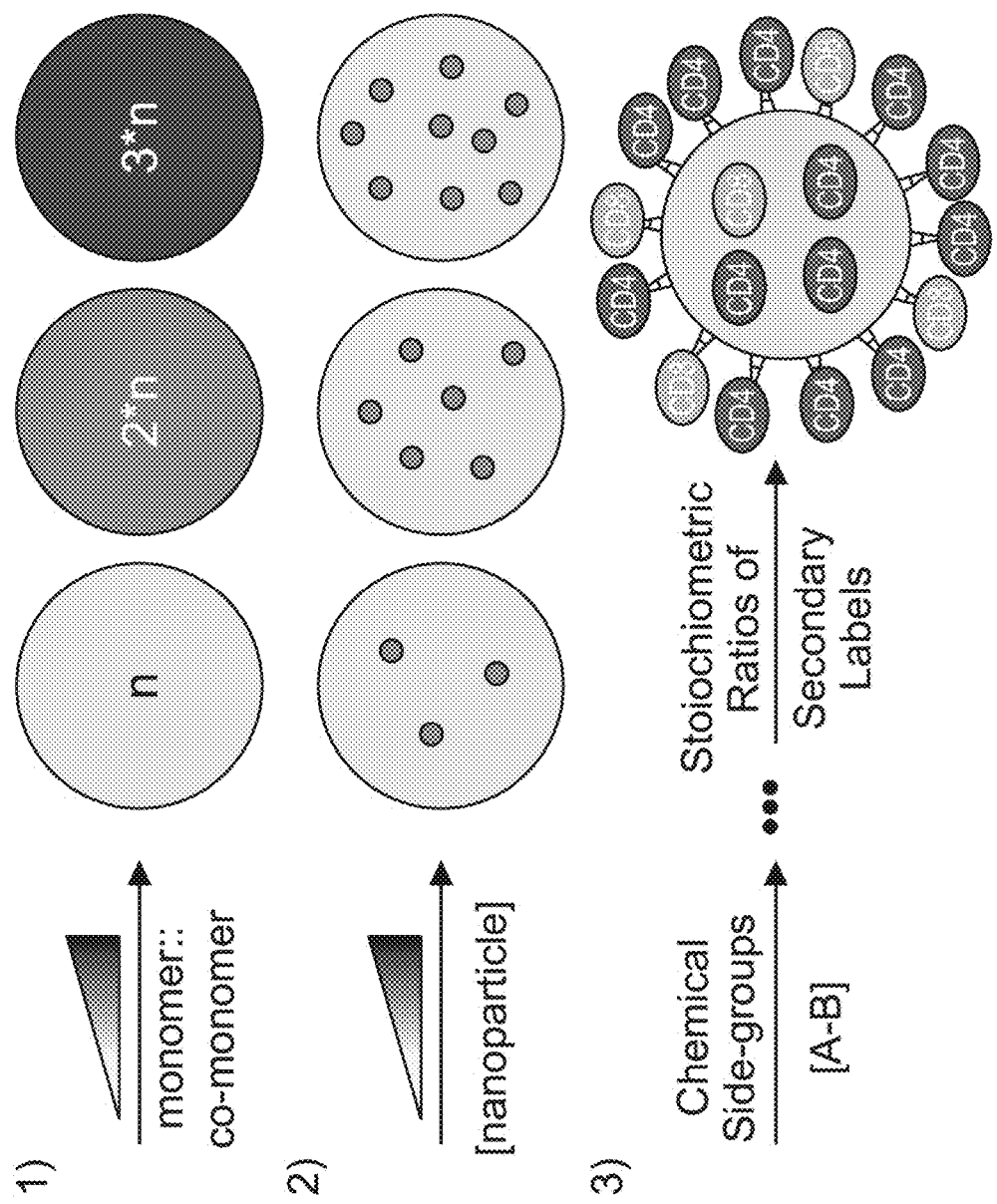
FIG. 4 illustrates the ability to independently tune each of the properties of an engineered hydrogel to match the passive optical scattering, autofluorescence, biomarker, and fluorescent properties of any target cell, according to some embodiments.

As depicted in FIG. 3, autofluorescent properties of hydrogel particles can be tuned in multiple dimensions to match cell-like background autofluorescence/spectral profiles of specific cell types (unlike polystyrene beads). Independent tuning of autofluorescence and forward scatter can be achieved by modulating/selectively modifying the co-monomer composition, the composition of nanoparticle additives, and/or the cross-linking density of the hydrogel particles. Cells are deconvolved using combinations of optical parameters such as FSC and SSC or secondary markers. Hydrogel particles are tuned to exactly match the SSC and FSC of specific cell types, unlike polystyrene beads which are limited in size and side scattering (as shown in FIGS. 1A(B) and 1B). FIG. 1A(A) shows that cells and the engineered hydrogels described herein are semi-transparent, allowing internal features to be resolved via side scatter (SSC). In contrast, as shown in FIG. 1A(B), polystyrene beads are opaque and have a defined side scatter determined by diameter. Hydrogel particles can further be functionalized with stoichiometrically tuned ratios of specific chemical side-groups and secondary labels, allowing any cell type to be precisely matched without suffering from biological noise as fixed cell lines do (see FIG. 4). Specifically, as shown in FIG. 4, the multiplexing capacity of functionalized hydrogels allows antigens and other biomarkers to be added to the hydrogel base polymer, adding further "cell-like" dimensions to the product.

Figure 6:
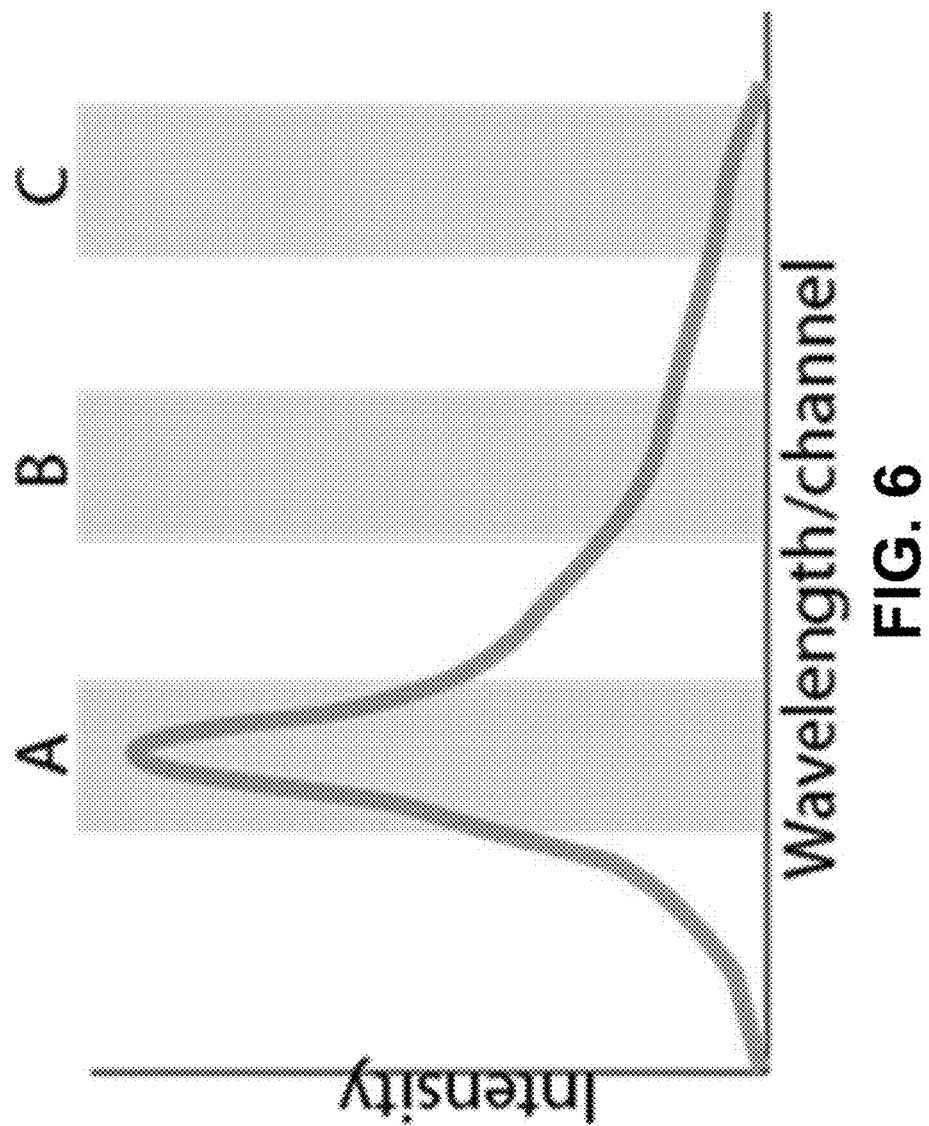
FIG. 6 is a plot of intensity versus wavelength/channel, demonstrating principles of fluorescence compensation.

Example 3: Comparison of Engineered Hydrogel Particles with Polystyrene Particles and Cells Hydrogel particles were formed using the methods described above, and measured in all fluorescent channels on a Beckman Coulter Cytoflex instrument. 5 µm polystyrene beads (BD Biosciences) were measured in parallel. Cells obtained from a commercial supplier were run in phosphate buffered saline and measured on a Beckman Coulter Cytoflex instrument. FIG. 6 is a plot of intensity versus wavelength/channel, demonstrating principles of fluorescence compensation. Specifically, FIG. 6 illustrates the concepts of fluorescence spillover and compensation. As shown in FIG. 6, the primary detection channel (A) shows the highest intensity for a model fluorophore, whereas channels B and C show spillover, or residual emission signal, from the single fluorophore. Such values can be subtracted from the measured fluorescence signal, when combining with other fluorophores that emit in these channels, to calculate a more accurate, or "true," fluorescence signal intensity.

Figure 7A:
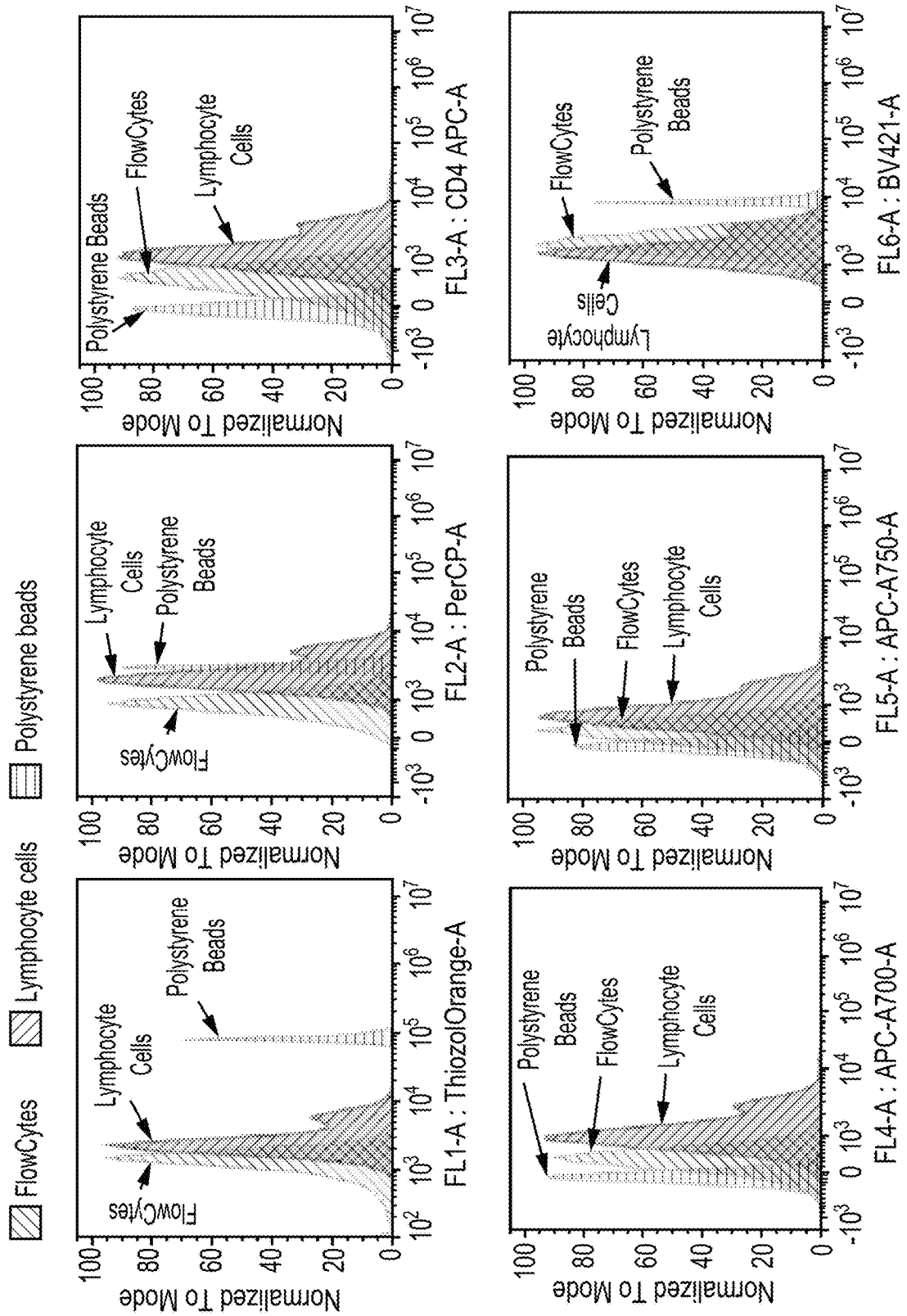
FIGS. 7A-7C include plots of data showing comparisons of human cells to polystyrene particles and hydrogel particles, across a range of fluorescent and spectral detectors, according to some embodiments.
Figure 7B:
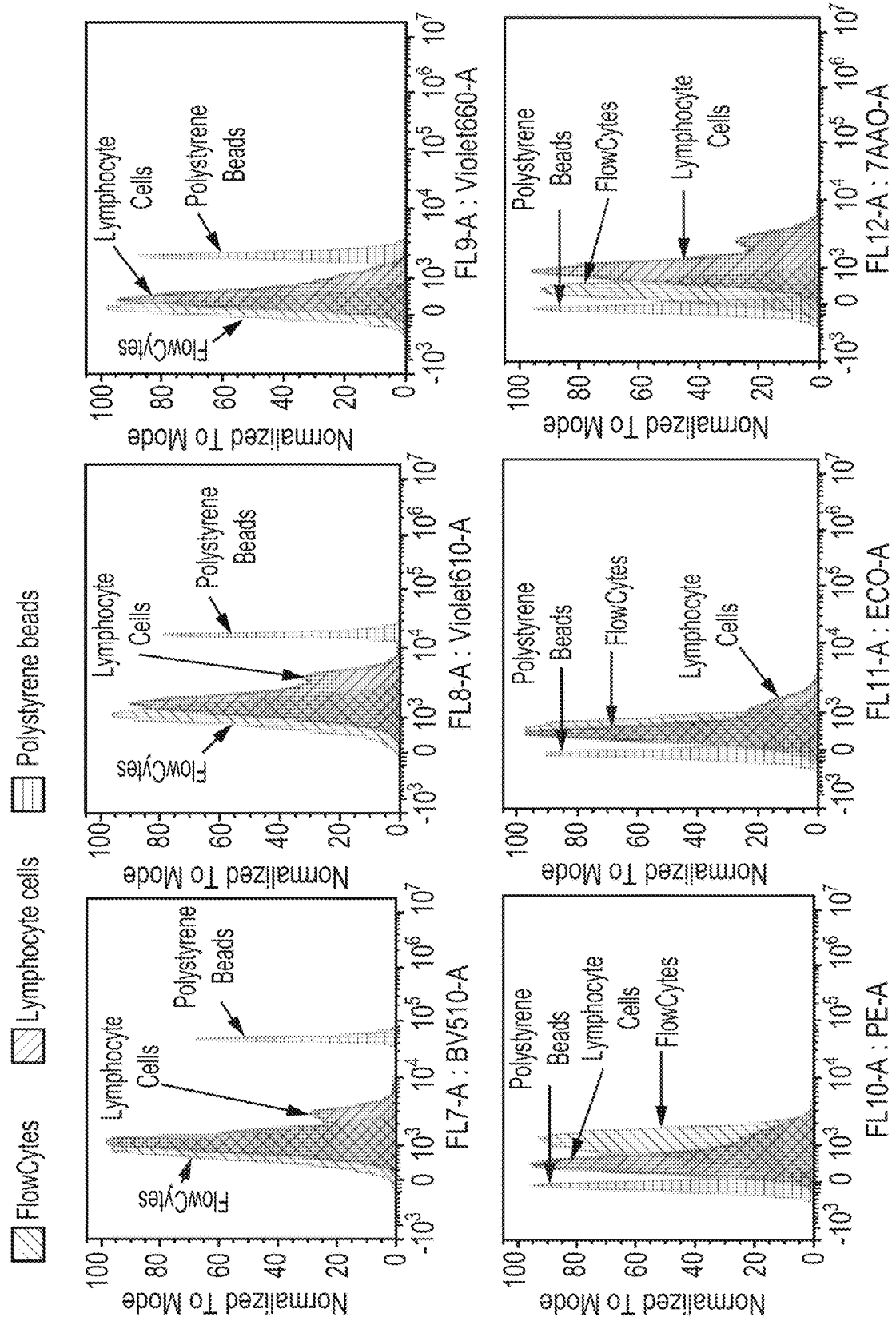
Figure 7C:
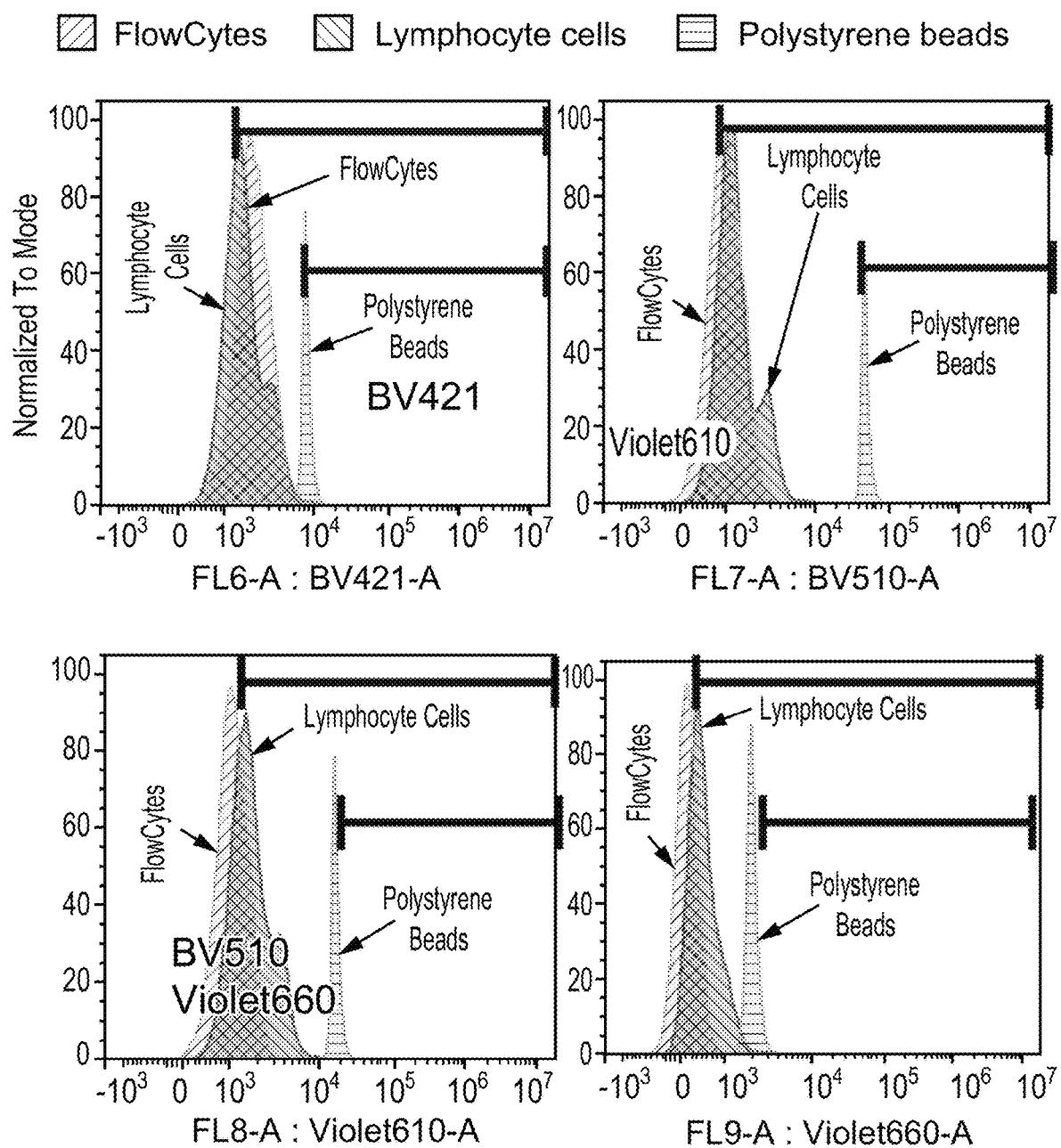

FIGS. 7A-7C facilitate comparisons of the fluorescence signatures between lymphocyte cells, polystyrene beads, and engineered hydrogel autofluorescence hydrogels of the present disclosure ("FlowCytes"). Each plot represents a standard fluorescence detection channel and an example antigen target or biological target named in that detection channel during common experiments. The channels are as follows:

Channel FL1-A-ThiozolOrange-A (a DNA-binding photosensitizer)
Channel FL2-A-PerCP-A (PerCP-conjugated antibodies, where PerCP is peridinin-chlorophyll-protein, a fluorescent complex)
Channel FL3-A-CD4 APC-A (cluster of differentiation (CD)4 Allophycocyanin (APC) antibody)
Channel FL4-A-APC-A700-A (conjugated antibody)
Channel FL5-A-APC-A750-A (conjugated antibody)
Channel FL6-A-BV421-1 (brilliant violet 421 antibody conjugate)
Channel FL7-A-BV510-A (brilliant violet 421 antibody conjugate)
Channel FL8-A-Violet610-A fluorescent nonaparticle dye
Channel FL9-A-Violet660-A fluorescent nonaparticle dye
Channel FL10-A-PE-A (phycoerythrin antibody)
Channel FL11-A-ECO-A
Channel FL12-A-7AAO-A (7-Aminoactinomycin D)

As shown in FIGS. 7A-7C, the FlowCytes exhibit more cell-like autofluorescence (i.e., their associated autofluorescence signatures are closer to those of the lymphocyte cells), as compared to the polystyrene beads. This allows for greater dynamic range to be measured on the same instrumentation and more accurate fluorescence compensation. For example, FIG. 7C shows that FlowCytes have lower autofluorescence in the ultraviolet and violet spectra, and are more cell-like (i.e., are more similar to the lymphocyte cells than the polystyrene beads). In addition, the FlowCytes have a comparatively high signal-to-noise ratio that facilitates better detection of poorly expressed or "dim" biomarkers by reducing the noise floor, and increasing the dynamic range of a given detector. The hydrogels described herein also allow for a synthetic bead product to be used with fluorochromes which excite or emit in the violet and ultraviolet ranges—a property that cannot be matched by current polystyrene-based products.

Figure 8A:
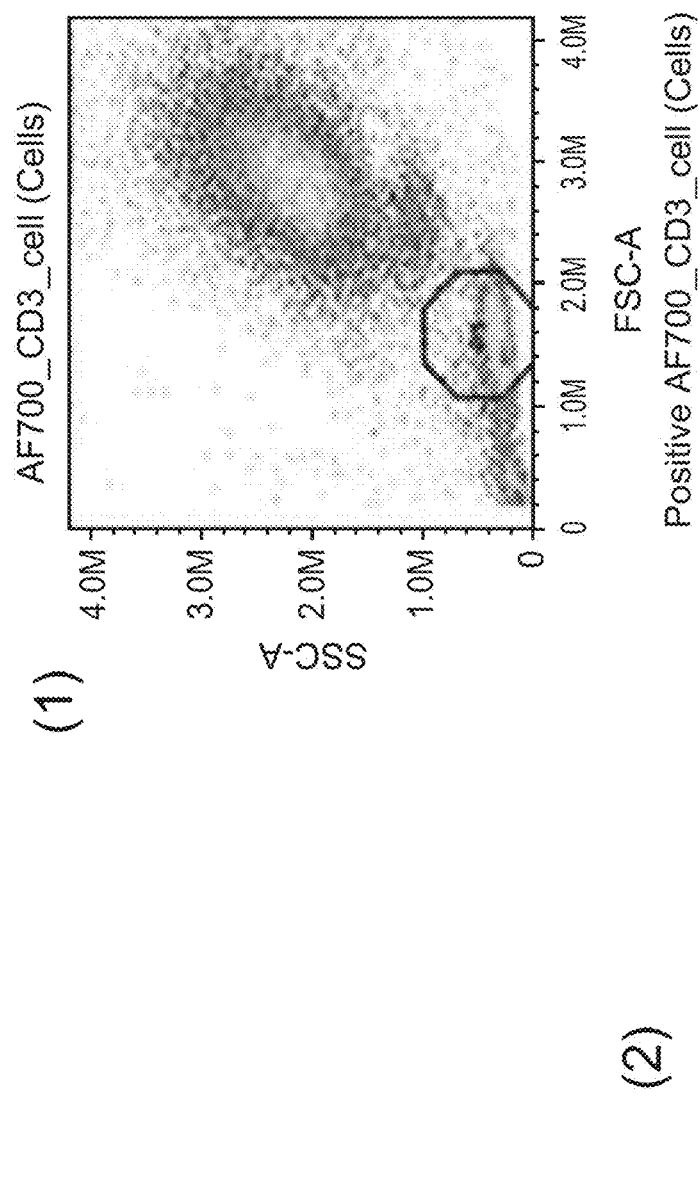
FIG. 8A is a spectral profile of lymphocytes stained with Alexa 700-modified antibodies ("Ab")
Figure 8A:
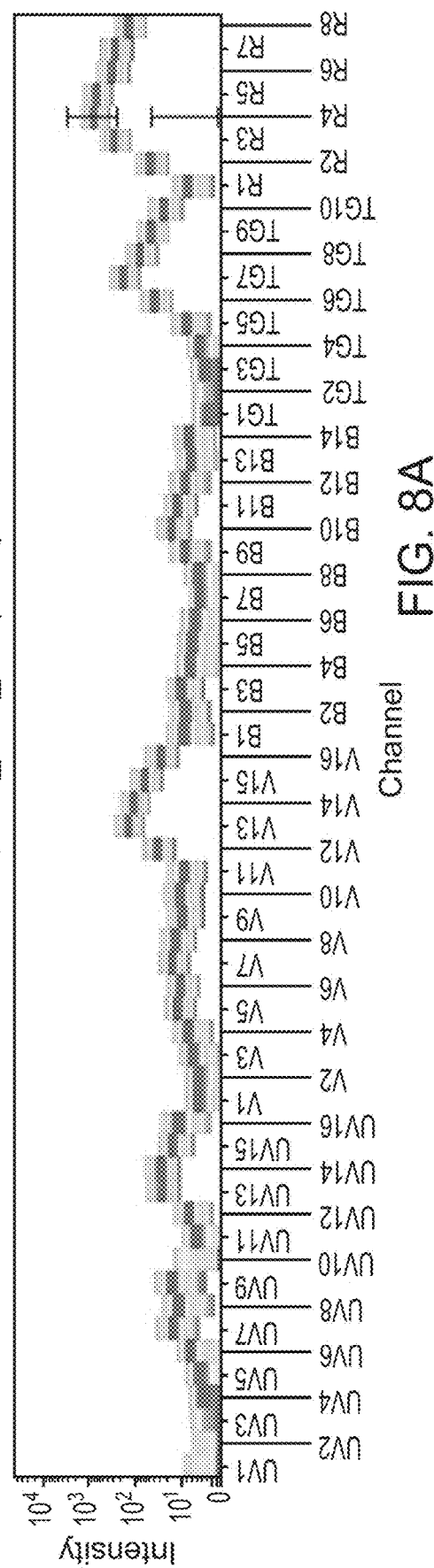
Figure 8B:
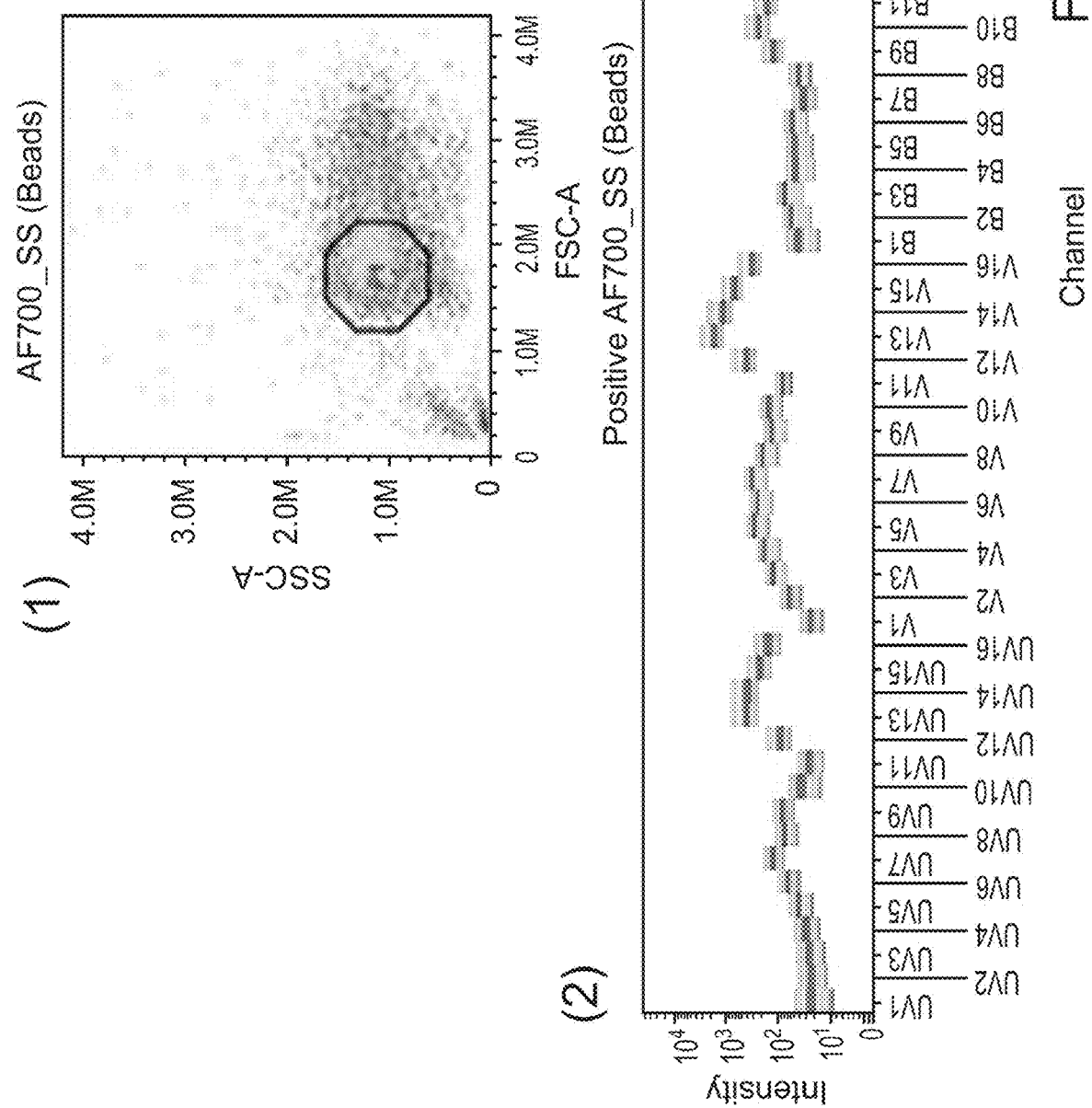
FIG. 8B is a spectral profile of hydrogel particles of the present disclosure, showing their alignment with the spectral profile of the pymphocytes of FIG. 8A, according to some embodiments.

FIG. 8A is a spectral profile of lymphocytes stained with Alexa 700-modified Ab, and FIG. 8B is a spectral profile of hydrogel particles (FlowCytes) of the present disclosure stained with Alexa 700-modified Ab, according to an embodiment. As shown in FIGS. 8A-8B, the stained FlowCytes have cell-like spectral signatures, with a peak-to-peak match of $r^2=1$.

Figure 9:
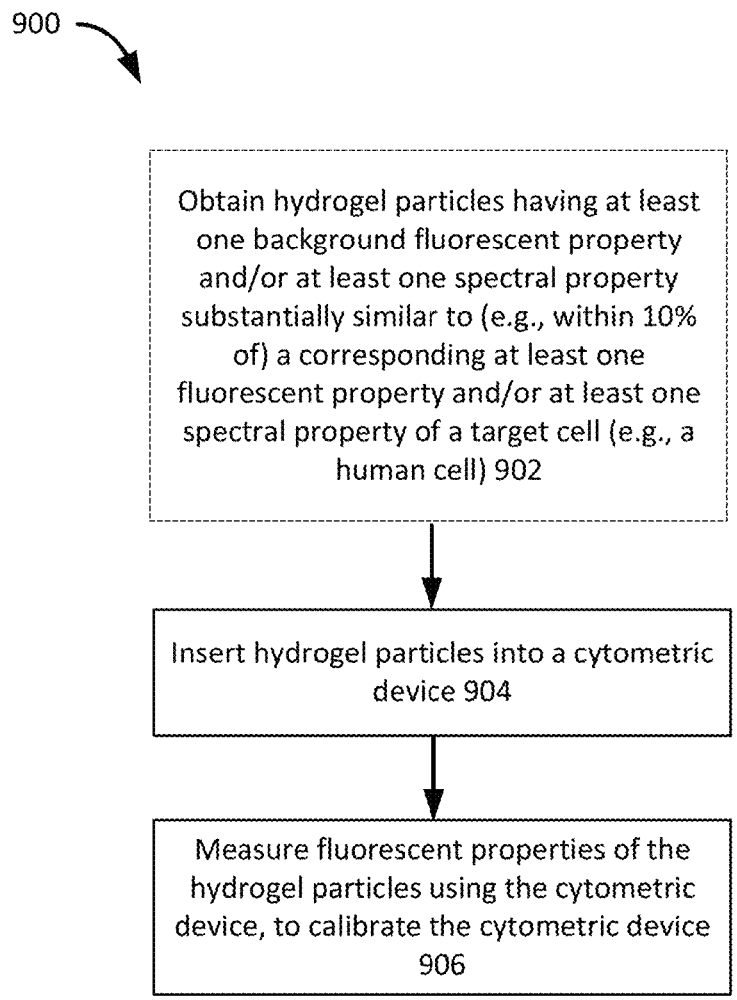
FIG. 9 is a flow diagram showing a method for calibrating a cytometric device for analysis of a target cell, in accordance with some embodiments.

FIG. 9 is a flow diagram showing a method for calibrating a cytometric device for analysis of a target cell, in accordance with some embodiments. As shown in FIG. 9, the method 900 optionally includes obtaining or producing, at 902, hydrogel particles having at least one background fluorescent property and/or at least one spectral property that is/are substantially similar to (e.g., within 10% of) a corresponding at least one fluorescent property and/or at least one spectral property of a target cell (e.g., a human cell). At 904, the method 900 includes inserting, into a cytometric device, at least one hydrogel particle (e.g., a plurality of hydrogel particles, optionally, in an aqueous medium or solution). The method also includes, at 906, measuring the fluorescent properties of the hydrogel particle using the cytometric device.

Figure 10:
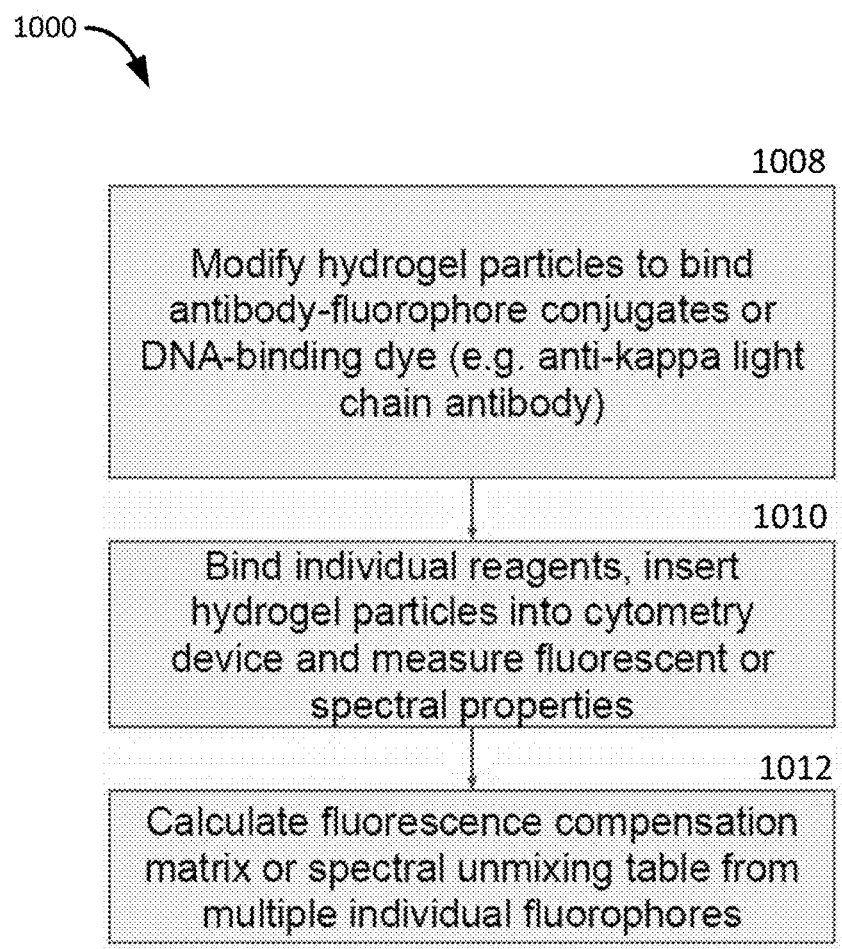
FIG. 10 is a flow diagram showing a process for calibration and the calculation of fluorescence compensation and/or spectral unmixing using hydrogels of the present disclosure, in accordance with some embodiments.

FIG. 10 is a flow diagram showing a process for calibration and the calculation of fluorescence compensation and spectral unmixing using hydrogels of the present disclosure. As shown in FIG. 10, the process 1000 includes modifying hydrogel particles, at 1008, to bind antibody-fluorophore conjugates or DNA_binding dye (e.g., anti-kappa light chain antibody) to the hydrogel particles. At 1010, individual reagents are bound and the hydrogel particles are inserted into a cytometry device for measurement of fluorescent and/or spectral properties thereof. A fluorescence compensation matrix and/or a spectral unmixing table is then calculated, at 1012, for multiple individual fluorophores.

Figure 11A:
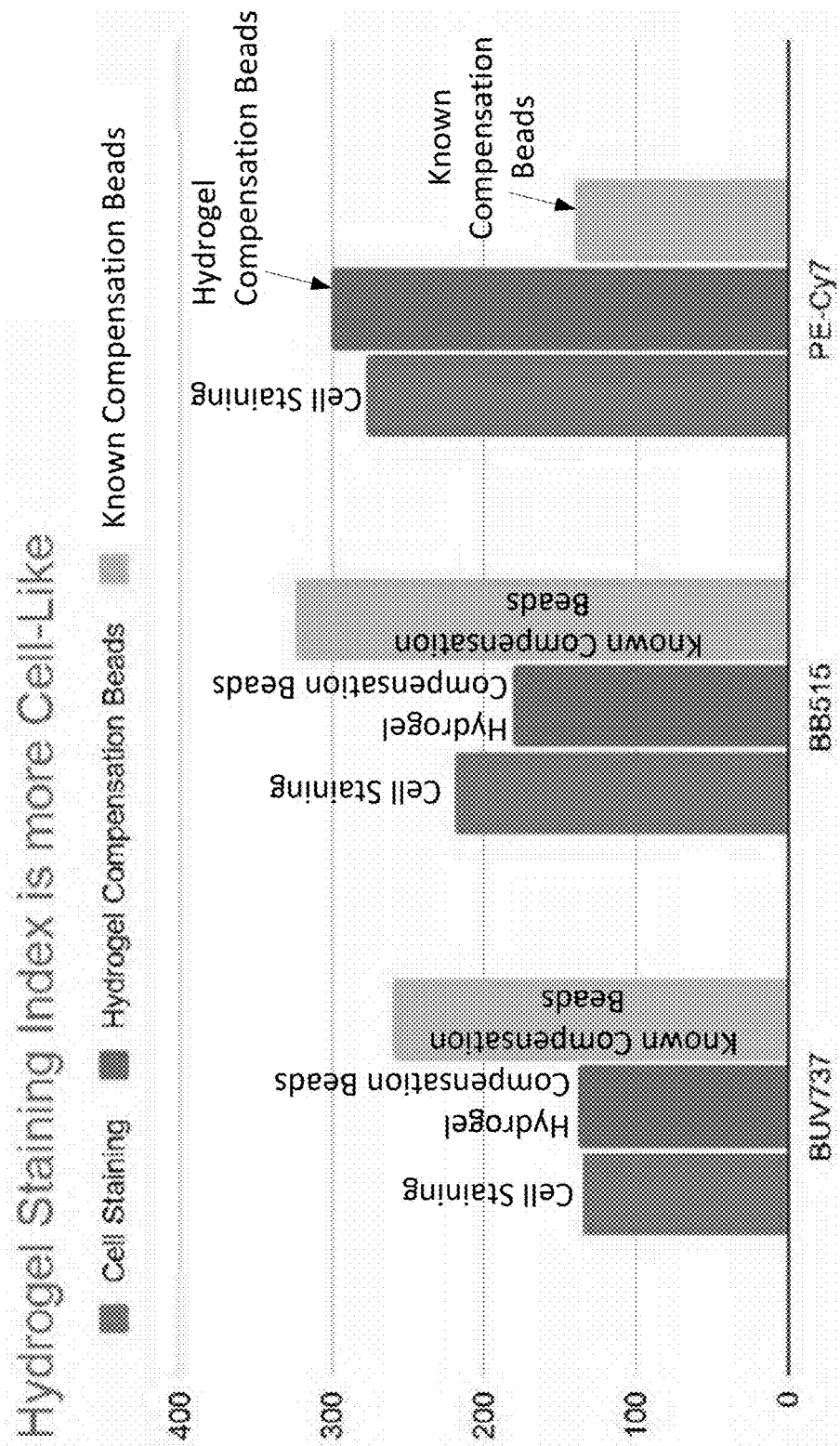
Figure 11B:
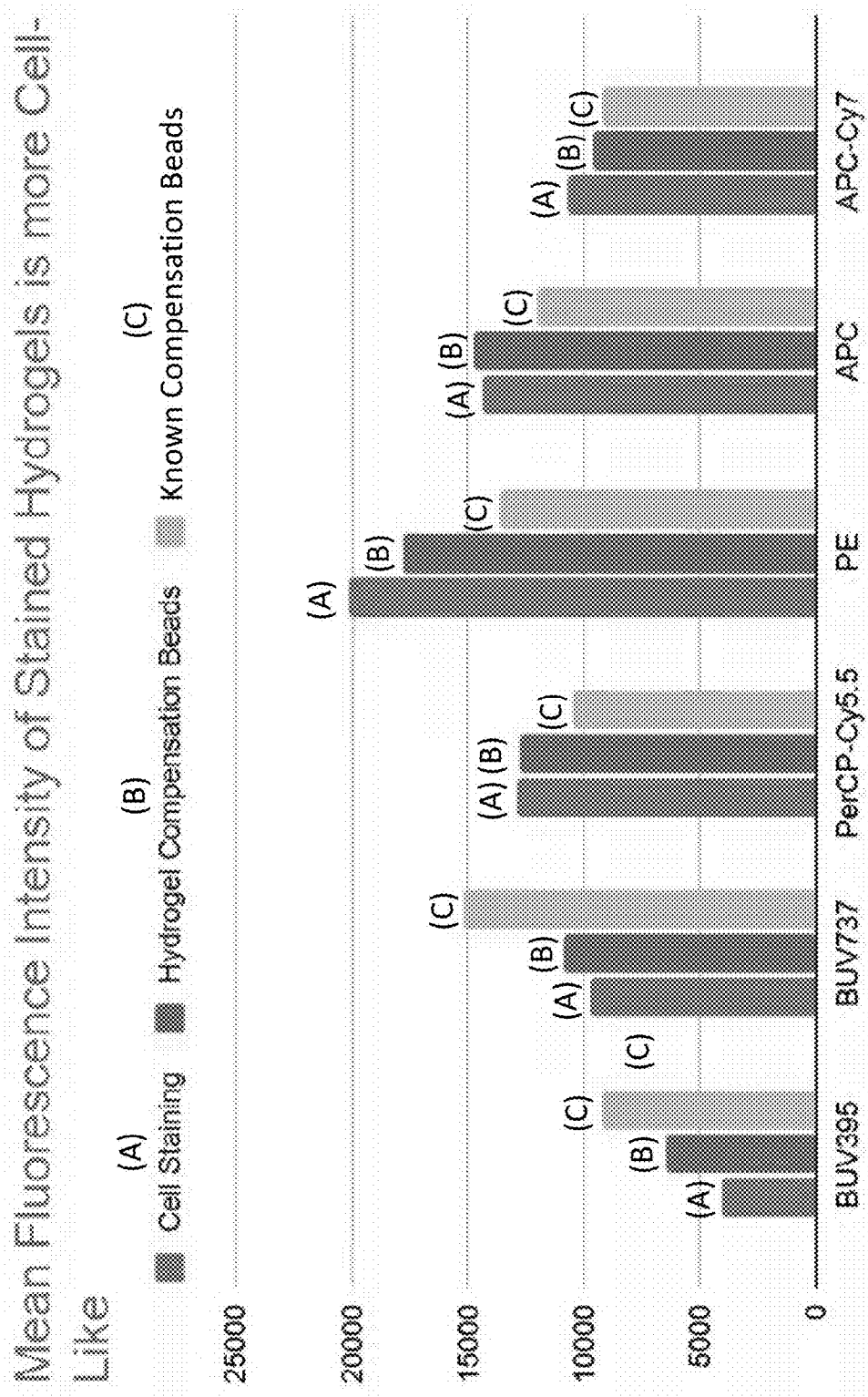
Figure 11C:
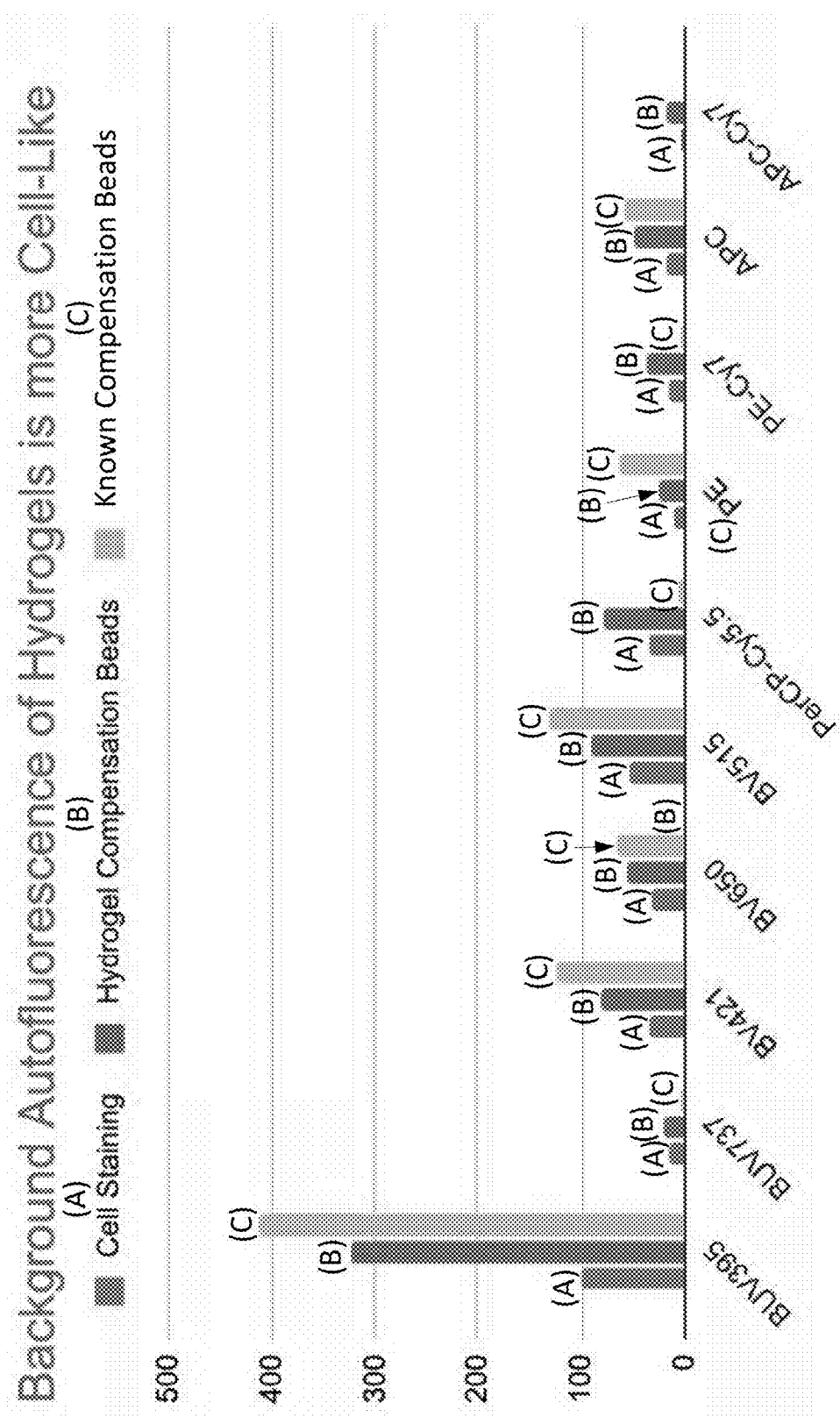

FIGS. 11A-11D are bar graphs showing a comparison between cell staining, hydrogel compensation beads, and known (polystyrene-based) bead products, according to some embodiments. In all depicted cases, the hydrogel beads of the present disclosure display more cell-like characteristics, leading to superior compensation and spectral unmixing performance. FIG. 11A describes the staining index and resolution performance of hydrogel compensation beads, as compared to known products. As can be seen in FIG. 11A, the staining indices of hydrogel compensation beads of the present disclosure are more cell-like than known compensation bead products. FIG. 11B describes the Mean Fluorescence Intensity (MFI) of stained hydrogels, as compared to known compensation products. As can be seen in FIG. 11B, the stained hydrogel compensation beads have more cell-like MFIs as compared to known compensation bead products. FIG. 11C describes the background autofluorescence of hydrogels, as compared to known compensation products. As can be seen in FIG. 11C, the unstained hydrogel compensation beads have more cell-like background autofluorescence as compared to known compensation bead products, across a wide range of channels. FIG. 11D describes the spillover performance of hydrogels, as compared to known compensation products. FIG. 11D shows that the fluorescence channel spillover is superior for hydrogel compensation beads of the present disclosure, as compared to known compensation bead products.

FIG. 12 is a chart showing two example methods of tuning autofluorescence of hydrogel particles: (1) modulating the percentage of a resonant co-monomer additive, or (2)

changing the crosslinking density of the hydrogel, according to some embodiments. FIG. 12 compares the autofluorescence of polystyrene and a cellular control with autofluorescence of these example hydrogel particles. As can be seen in the lefthand table of FIG. 12, a hydrogel particle prepared with 5% resonant co-monomer additive has a cell-like autofluorescence (1050), whereas the polystyrene control has an autofluorescence that is undesirably high (9781). As can be seen in the righthand table of FIG. 12, a hydrogel particle prepared with 10% crosslinking density has a cell-like autofluorescence (1104), whereas the polystyrene control has an autofluorescence that is undesirably high (9781).

In some embodiments, a composition includes an aqueous solution and a hydrogel particle suspended in the aqueous solution. The hydrogel particle has at least one of a background autofluorescence that is substantially similar to that of a target cell or a spectral profile that is substantially similar to that of a target cell. These specific properties have been engineered using a combination of co-monomer additives, adjusted curing kinetics (which are impacted by, and thus can be adjusted by modifying, time, temperature, and chemical accelerants), and low-concentration nanoparticle additives. These properties (autofluorescence and spectral profile) are characterized using non-passive optical excitation channels, distinguishing it from passive optical features (such as SSC and FSC).

The hydrogel particle can also have an SSC that is within 10% of that of a target cell, as measured by a cytometric device. The hydrogel particle can also have an FSC that is within 10% of that of a target cell, as measured by a cytometric device.

The hydrogel particle can also have a refractive index of greater than about 1.15, or greater than about 1.3, or greater than about 1.7.

The hydrogel particle can also have a diameter of less than about 100 µm, or less than about 10 µm, or less than about 1 µm.

In some embodiments, the hydrogel particle contains polymer nanoparticle additives.

In some embodiments, the hydrogel particle is chemically functionalized. For example, the hydrogel particle can include a free amine group.

In some embodiments, the hydrogel particle comprises allylamine.

In some embodiments, the target cell is an immune cell.

In some embodiments, the hydrogel particle is produced by polymerizing a droplet.

In some embodiments, the hydrogel particle is produced by polymerizing a droplet and the hydrogel particle is subsequently modified by conjugating or attaching a fluorophore/fluorochrome. The modified hydrogel particle can have a fluorescence profile that matches (e.g., that is substantially similar to, or that is within 10% of) a fluorescence profile of the target cell.

In some embodiments, a population of hydrogel particles includes a plurality of hydrogel particles, each hydrogel particle from the plurality of hydrogel particles having at least one of a background autofluorescence or a spectral profile that is substantially similar to a background autofluorescence or a spectral profile of a target cell. The population of hydrogel particles can be substantially monodisperse. In some such embodiments, no more than 10% of the hydrogel particles have an average diameter greater than about 10% of the average diameter of the population of hydrogel particles.

In some embodiments, a method includes calibrating a cytometric device for analysis of a target cell, by inserting, into the cytometric device, at least one hydrogel particle (e.g., a plurality of hydrogel particles, optionally, in an aqueous medium or solution). The at least one hydrogel particles has at least one of a background fluorescent property or a spectral property that is substantially similar to the at least one of a background fluorescent property (e.g., autofluorescence) or a spectral property of the target cell. The method also includes measuring at least one property (e.g., calibration-related properties) of the hydrogel particle using the cytometric device. The at least one property can include one or more of: inter-laser delay, fluorescence response, sort timing, or fluorescence compensation. The method optionally also includes adjusting one of a fluorescent compensation or a spectral unmixing based on the measured properties. Spectral unmixing is the process of decomposing a spectral signature of a mixed pixel into a set of endmembers and their corresponding abundances. The calculation of compensation and spectral unmixing using the described cell-like reagents allows for an expanded range of fluorophores to be multiplexed by reducing the noise and increasing the cell-like accuracy of a given fluorophore. In some embodiments, the method also includes, prior to inserting the hydrogel particle into the cytometric device: binding a reagent containing a fluorophore to the hydrogel particle to form a complex, measuring at least one property of the complex, and calculating a fluorescent compensation or a spectral unmixing based on the at least one measured property. Optionally, the method also includes using the modified hydrogel particle to assess a viability of the target cell.

In some embodiments, the hydrogel particle has been modified to bind to an antibody that is bound to a conjugated fluorophore (e.g., a fluorochrome).

In some embodiments, the hydrogel particle is a modified hydrogel particle that has been modified to bind to at least one of an intercalating nucleic acid labeling reagent or an amine-reactive nucleic acid labeling reagent.

The hydrogel particle can have an SSC within 10% of that of a target cell, as measured by a cytometric device. Alternatively or in addition, the hydrogel particle can have an FSC within 10% of that of a target cell, as measured by a cytometric device.

In some embodiments, the hydrogel particle can have a refractive index of greater than about 1.15, or greater than about 1.3, or greater than about 1.7.

In some embodiments, the hydrogel particle can have a diameter of less than about 100 µm, or a diameter of less than about 10 µm, or a diameter of less than about 1 µm.

In some embodiments, the hydrogel particle includes polymer nanoparticle additives.

In some embodiments, the hydrogel particle is a chemically functionalized hydrogel particle.

In some embodiments, the hydrogel particle comprises a free amine group.

In some embodiments, the hydrogel particle comprises allylamine.

In some embodiments, the target cell is an immune cell.

In some embodiments, the method also includes polymerizing a droplet to produce the hydrogel particle.

In some embodiments, the hydrogel particle is a hydrogel particle that has been modified by conjugating or attaching one of a fluorophore or a fluorochrome, and the modified hydrogel particle matches the fluorescence or spectral profile of a cell.

In some embodiments, a method includes calculating a compensation value for a cytometric measurement of a target cell and modifying the cytometric measurement of the target cell based on the compensation value. The calculating the compensation value for the cytometric measurement of the target cell includes inserting, into the cytometric device and at a first time, a first hydrogel particle. The first hydrogel particle has at least one of a background fluorescent property or a spectral property that is substantially similar to the at least one of a background fluorescent property or a spectral property of the target cell. At least one property of the first hydrogel particle is measured using the cytometric device. The calculating also includes inserting, into the cytometric device and at a second time different from the first time, a second hydrogel particle, and measuring at least one property of the second hydrogel particle using the cytometric device. The calculating also includes comparing the measured at least one property of the first hydrogel particle and the measured at least one property of the second hydrogel particle to determine the compensation value.

In some embodiments, a method includes calculating a plurality of adjustment values for a cytometric measurement of a target cell, and modifying the cytometric measurement of the target cell based on the plurality of adjustment values. The calculating the plurality of adjustment values for the cytometric measurement of the target cell includes inserting, into the cytometric device, two hydrogel particles, a first hydrogel particle from the hydrogel particles having at least one of a background fluorescent property or a spectral property that is substantially similar to the at least one of a background fluorescent property or a spectral property of the target cell, and a second hydrogel particle from the hydrogel particles that is one of configured to bind to a reagent or pre-bound to the reagent, the reagent being a reagent that generates at least one of a fluorescent signal different from the background fluorescent property or a spectral signal different from the spectral property. The calculating the plurality of adjustment values for the cytometric measurement of the target cell also includes measuring at least one property of the first hydrogel particle and at least one property of the second hydrogel particle using the cytometric device, and comparing the measured at least one property of the first hydrogel particle and the measured at least one property of the second hydrogel particle to determine a fluorescent overlap with at least one additional reagent and a spectral overlap with the at least one additional reagent. The cytometric measurement of the target cell is then modified based on the plurality of adjustment values (e.g., including or based on the fluorescent overlap with at least one additional reagent and/or the spectral overlap with the at least one additional reagent).

Although shown and described herein as being used in the context of cytometric device calibration and cytometric measurement compensation, the cell-like hydrogel particles described herein can also be used in other applications to improve their performance and/or accuracy. For example, additional applications compatible with the cell-like hydrogel particles of the present disclosure include, but are not limited to: (1) setting of a lower limit of detection ("LLOD") of an instrument (examples of which include, but are not limited to: a flow cytometer, a hematology analyzer, a cell analyzer, or an image-based cytomer), to determine true signal-to-noise ratios for dim or poorly-expressed biomarkers; (2) photomultiplier tube ("PMT") gain adjustments to capture cell-like fluorescence linearity; (3) mean fluorescence intensity ("MFI") calculations, and (4) instrument set-up and quality control ("QC") for fluorescence detection (active optical properties, as opposed to passive optical properties).

While various specific embodiments have been illustrated and described, it will be appreciated that various changes can be made without departing from the spirit and scope of the invention.

As used herein throughout the specification and in the appended claims, the following terms and expressions are intended to have the following meanings:

The indefinite articles "a" and "an" and the definite article "the" are intended to include both the singular and the plural, unless the context in which they are used clearly indicates otherwise.

"At least one" and "one or more" are used interchangeably to mean that the article may include one or more than one of the listed elements.

Unless otherwise indicated, it is to be understood that all numbers expressing quantities, ratios, and numerical properties of ingredients, reaction conditions, and so forth, used in the specification and claims are contemplated to be able to be modified in all instances by the term "about".

As used herein, the terms "about" and "approximately" generally mean plus or minus 10% of the value stated, for example about 250 μm would include 225 μm to 275 μm, about 1,000 μm would include 900 μm to 1,100 μm.

In this disclosure, references to items in the singular should be understood to include items in the plural, and vice versa, unless explicitly stated otherwise or clear from the context. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth. The use of any and all examples, or exemplary language ("e.g.," "such as," "including," or the like) provided herein, is intended merely to better illuminate the embodiments and does not pose a limitation on the scope of the embodiments or the claims.

The invention claimed is:

1. A composition comprising: a hydrogel particle having
   a) a polymer matrix; and
   b) a background fluorescent property that is substantially similar to a background fluorescent property of a target cell;
wherein the hydrogel particle is configured to bind to an antibody that is bound to a conjugated fluorophore.

2. The composition of claim 1, wherein the hydrogel particle comprises a monomer selected from hydroxyethyl methacrylate, ethyl methacrylate, 2-hydroxyethyl methacrylate (HEMA), propylene glycol methacrylate, acrylamide, N-vinylpyrrolidone (NVP), methyl methacrylate, glycidyl methacrylate, glycerol methacrylate (GMA), glycol methacrylate, ethylene glycol, fumaric acid, 2-hydroxyethyl methacrylate, hydroxyethoxyethyl methacrylate, hydroxydiethoxyethyl methacrylate, methoxyethyl methacrylate, methoxyethoxyethyl methacrylate, methoxydiethoxyethyl methacrylate, poly(ethylene glycol) methacrylate, methoxypoly(ethylene glycol) methacrylate, methacrylic acid, sodium methacrylate, glycerol methacrylate, hydroxypropyl methacrylate, hydroxybutyl methacrylate, phenyl acrylate, phenyl methacrylate, benzyl acrylate, benzyl methacrylate, 2-phenylethyl acrylate, 2-phenylethyl methacrylate, 2-phenoxyethyl acrylate, 2-phenoxyethyl methacrylate, phenylthioethyl acrylate, phenylthioethyl methacrylate, 2,4,6-tribromophenyl acrylate, 2,4,6-tribromophenyl methacrylate, pentabromophenyl acrylate, pentabromophenyl methacrylate, pentachlorophenyl acrylate, pentachlorophenyl methacrylate, 2,3-dibromopropyl acrylate, 2,3-dibromopropyl methacrylate, 2-naphthyl acrylate, 2-naphthyl methacrylate, 4-methoxybenzyl acrylate, 4-methoxybenzyl methacrylate, 2-benzyloxyethyl acrylate, 2-benzyloxyethyl methacrylate, 4-chlorophenoxyethyl acrylate, 4-chlorophenoxyethyl methacrylate, 2-phenoxyethoxyethyl 2-acrylate, phenoxyethoxyethyl methacrylate, N-phenyl acrylamide, N-phenyl methacrylamide, N-benzyl acrylamide, N-benzyl methacrylamide, N,N-dibenzyl acrylamide, N,N-dibenzyl methacrylamide, N-diphenylmethyl acrylamide N-(4-methylphenyl) methyl acrylamide, N-1-naphthyl acrylamide, N-4-nitrophenyl acrylamide, N-(2-phenylethyl)acrylamide, N-triphenylmethyl acrylamide, N-(4-hydroxyphenyl) acrylamide, N,N-methylphenyl acrylamide, N,N-phenyl phenylethyl acrylamide, N-diphenylmethyl methacrylamide, N-(4-methyl phenyl)methyl methacrylamide, N-1-naphthyl methacrylamide, N-4-nitrophenyl methacrylamide, N-(2-phenylethyl)methacrylamide, N-triphenylmethyl methacrylamide, N-(4-hydroxyphenyl)methacrylamide, N,N-methylphenyl methacrylamide, N,N'-phenyl phenylethyl methacrylamide, N-vinyl carbazole, 4-vinylpyridine, 2-vinylpyridine, or a combination thereof.

3. The composition of claim 1, wherein the conjugated fluorophore is a fluorochrome.

4. The composition of claim 1, wherein the hydrogel particle is configured to bind to at least one of an intercalating nucleic acid labeling reagent or an amine-reactive labeling reagent.

5. The composition of claim 1, wherein the hydrogel particle comprises a fluorophore.

6. The composition of claim 1, wherein the hydrogel particle has a refractive index of greater than about 1.15.

7. The composition of claim 1, wherein the hydrogel particle has a diameter of less than about 100 µm.

8. The composition of claim 1, wherein the hydrogel particle has a diameter of less than about 10 µm.

9. The composition of claim 1, wherein the hydrogel particle contains polymer nanoparticle additives.

10. The composition of claim 1, wherein the hydrogel particle is a chemically functionalized hydrogel particle.

11. The composition of claim 1, wherein the hydrogel particle comprises a free amine group.

12. The method of claim 1, wherein the hydrogel particle comprises allylamine.

13. The composition of claim 1, wherein the target cell is an immune cell.

14. The composition of claim 1, wherein the hydrogel particle has been modified to match a fluorescence profile of the target cell.

15. The composition of claim 1, wherein the at least one of the background fluorescent property includes one of inter-laser delay, fluorescence response, or sort timing.

16. The composition of claim 1, wherein the target cell is a human cell.

17. A composition comprising: a hydrogel particle having
a) a polymer matrix; and
b) a background fluorescent property that is substantially similar to a background fluorescent property of a target cell;
wherein the hydrogel particle is configured to bind to at least one of an intercalating nucleic acid labeling reagent or an amine-reactive labeling reagent.

18. The composition of claim 17, wherein the hydrogel particle comprises a monomer selected from hydroxyethyl methacrylate, ethyl methacrylate, 2-hydroxyethyl methacrylate (HEMA), propylene glycol methacrylate, acrylamide, N-vinylpyrrolidone (NVP), methyl methacrylate, glycidyl methacrylate, glycerol methacrylate (GMA), glycol methacrylate, ethylene glycol, fumaric acid, 2-hydroxyethyl methacrylate, hydroxyethoxyethyl methacrylate, hydroxydiethoxyethyl methacrylate, methoxyethyl methacrylate, methoxyethoxyethyl methacrylate, methoxydiethoxyethyl methacrylate, poly(ethylene glycol) methacrylate, methoxypoly(ethylene glycol) methacrylate, methacrylic acid, sodium methacrylate, glycerol methacrylate, hydroxypropyl methacrylate, hydroxybutyl methacrylate, phenyl acrylate, phenyl methacrylate, benzyl acrylate, benzyl methacrylate, 2-phenylethyl acrylate, 2-phenylethyl methacrylate, 2-phenoxyethyl acrylate, 2-phenoxyethyl methacrylate, phenylthioethyl acrylate, phenylthioethyl methacrylate, 2,4,6-tribromophenyl acrylate, 2,4,6-tribromophenyl methacrylate, pentabromophenyl acrylate, pentabromophenyl methacrylate, pentachlorophenyl acrylate, pentachlorophenyl methacrylate, 2,3-dibromopropyl acrylate, 2,3-dibromopropyl methacrylate, 2-naphthyl acrylate, 2-naphthyl methacrylate, 4-methoxybenzyl acrylate, 4-methoxybenzyl methacrylate, 2-benzyloxyethyl acrylate, 2-benzyloxyethyl methacrylate, 4-chlorophenoxyethyl acrylate, 4-chlorophenoxyethyl methacrylate, 2-phenoxyethoxyethyl acrylate, 2-phenoxyethoxyethyl methacrylate, N-phenyl acrylamide, N-phenyl methacrylamide, N-benzyl acrylamide, N-benzyl methacrylamide, N,N-dibenzyl acrylamide, N,N-dibenzyl methacrylamide, N-diphenylmethyl acrylamide N-(4-methylphenyl) methyl acrylamide, N-1-naphthyl acrylamide, N-4-nitrophenyl acrylamide, N-(2-phenylethyl)acrylamide, N-triphenylmethyl acrylamide, N-(4-hydroxyphenyl) acrylamide, N,N-methylphenyl acrylamide, N,N-phenyl phenylethyl acrylamide, N-diphenylmethyl methacrylamide, N-(4-methyl phenyl)methyl methacrylamide, N-1-naphthyl methacrylamide, N-4-nitrophenyl methacrylamide, N-(2-phenylethyl)methacrylamide, N-triphenylmethyl methacrylamide, N-(4-hydroxyphenyl)methacrylamide, N,N-methylphenyl methacrylamide, N,N'-phenyl phenylethyl methacrylamide, N-vinyl carbazole, 4-vinylpyridine, 2-vinylpyridine, or a combination thereof.

19. The composition of claim 17, wherein the hydrogel particle comprises a fluorophore.

20. The composition of claim 17, wherein the hydrogel particle has a refractive index of greater than about 1.15.

21. The composition of claim 17, wherein the hydrogel particle has a diameter of less than about 100 µm.

22. The composition of claim 17, wherein the hydrogel particle has a diameter of less than about 10 µm.

23. The composition of claim 17, wherein the hydrogel particle contains polymer nanoparticle additives.

24. The composition of claim 17, wherein the hydrogel particle is a chemically functionalized hydrogel particle.

25. The composition of claim 17, wherein the hydrogel particle comprises a free amine group.

26. The method of claim 17, wherein the hydrogel particle comprises allylamine.

27. The composition of claim 17, wherein the target cell is an immune cell.

28. The composition of claim 17, wherein the hydrogel particle has been modified to match a fluorescence profile of the target cell.

29. The composition of claim 17, wherein the at least one of the background fluorescent property includes one of inter-laser delay, fluorescence response, or sort timing.

30. The composition of claim 17, wherein the target cell is a human cell.

* * * * *